United States Patent
Jooste et al.

(10) Patent No.: US 9,680,831 B2
(45) Date of Patent: Jun. 13, 2017

(54) DATA PERMISSION MANAGEMENT FOR WEARABLE DEVICES

(71) Applicant: Verily Life Sciences LLC, Mountain View, CA (US)

(72) Inventors: Sarel Kobus Jooste, Novato, CA (US); David Andrew Gibson, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 34 days.

(21) Appl. No.: 14/447,466

(22) Filed: Jul. 30, 2014

(65) Prior Publication Data

US 2016/0034696 A1 Feb. 4, 2016

(51) Int. Cl.
| | |
|---|---|
| G06F 21/62 | (2013.01) |
| H04L 29/06 | (2006.01) |
| G06F 1/16 | (2006.01) |
| H04W 12/08 | (2009.01) |
| A61B 5/00 | (2006.01) |

(52) U.S. Cl.
CPC ............ *H04L 63/10* (2013.01); *A61B 5/681* (2013.01); *G06F 1/163* (2013.01); *G06F 21/6245* (2013.01); *G06F 21/6254* (2013.01); *H04W 12/08* (2013.01)

(58) Field of Classification Search
None
See application file for complete search history.

(56) References Cited

U.S. PATENT DOCUMENTS

| | | |
|---|---|---|
| 2003/0115142 A1 | 6/2003 | Brickell et al. |
| 2003/0174049 A1 | 9/2003 | Beigel et al. |
| 2005/0204149 A1 | 9/2005 | Watanabe |
| 2006/0074280 A1* | 4/2006 | Martis ................ A61B 3/005 600/310 |
| 2008/0216171 A1 | 9/2008 | Sano et al. |

(Continued)

FOREIGN PATENT DOCUMENTS

WO 2014/040175 A1 3/2014

OTHER PUBLICATIONS

International Search Report and Written Opinion of International Application No. PCT/US2015/042266, dated Nov. 4, 2015.

*Primary Examiner* — Michael R Vaughan
(74) *Attorney, Agent, or Firm* — McDonnell Boehnen Hulbert & Berghoff LLP

(57) ABSTRACT

Methods and apparatus for providing rule-based access to data stored on wearable devices are provided. A wearable computing device can store data that includes data about a wearer of the wearable computing device. The wearable computing device can receive a request for a portion of the stored data. The wearable computing device can determine a designated role associated with the request for the portion of the stored data. The wearable computing device can determine one or more rules regarding access to the portion of the stored data based on the designated role. The wearable computing device can determine a response to the request for the portion of the stored data by at least: determining whether the request is validated by at least applying the one or more rules to the request, and after determining that the request is validated, providing the requested portion of the stored data.

20 Claims, 17 Drawing Sheets

(56) References Cited

U.S. PATENT DOCUMENTS

| | | | | |
|---|---|---|---|---|
| 2008/0270185 | A1* | 10/2008 | Gossler | G06Q 50/22 705/2 |
| 2008/0303638 | A1* | 12/2008 | Nguyen | G06F 19/3462 340/10.42 |
| 2009/0271635 | A1 | 10/2009 | Liu et al. | |
| 2012/0221464 | A1* | 8/2012 | Pasquero | H04L 63/0492 705/39 |
| 2012/0254737 | A1* | 10/2012 | Levien | G06F 3/0487 715/249 |
| 2013/0159519 | A1 | 6/2013 | Hochberg et al. | |
| 2014/0085101 | A1 | 3/2014 | Rahman et al. | |
| 2014/0089673 | A1* | 3/2014 | Luna | H04L 63/0861 713/186 |
| 2014/0373100 | A1* | 12/2014 | Poiesz | G06F 21/30 726/4 |
| 2015/0033286 | A1* | 1/2015 | Shahidzadeh | H04L 63/10 726/1 |
| 2015/0088007 | A1* | 3/2015 | Bardy | A61B 5/0022 600/484 |
| 2015/0135284 | A1* | 5/2015 | Bogard | H04L 63/107 726/5 |
| 2015/0186636 | A1* | 7/2015 | Tharappel | G06F 21/32 726/8 |
| 2015/0206364 | A1* | 7/2015 | Agrafioti | G06F 21/40 340/5.82 |
| 2015/0223731 | A1* | 8/2015 | Sahin | A61B 5/16 600/301 |
| 2015/0317855 | A1* | 11/2015 | Sezan | G07C 9/00158 340/5.52 |
| 2015/0324794 | A1* | 11/2015 | Vadura | G06Q 20/3274 705/21 |
| 2015/0379255 | A1* | 12/2015 | Konanur | G06F 21/35 726/19 |
| 2016/0071343 | A1* | 3/2016 | Agrafioti | G06F 21/40 340/5.52 |
| 2016/0183812 | A1* | 6/2016 | Zhang | A61B 5/02055 600/301 |

\* cited by examiner

Example Wearable Device Data 1010

| Data Type | Sensitive Data? | Example Data |
|---|---|---|
| 1012 Physiological | Yes | Heart rate, breathing rate, blood sugar |
| 1014 Aggregated | Usually not | Non-real-time physiological data without ID |
| 1016 Application | Depends on application | Internet data, documents, audio, video |
| 1018 Networking | Usually not | Network addresses |
| 1020 Access Rule | Yes | Allow/deny access to data |
| 1022 System | Usually | Storage allocation, thread/process data |

Example Wearable Device Roles 1030

| | Data Access | | | | | |
|---|---|---|---|---|---|---|
| Role | Physio? | Agg? | App? | Network? | Rules? | Other? |
| 1032 Global | Y | Y | Y | Y | Y | Y |
| 1034 Manager | some/all | Y | some | some/all | Y | some/all |
| 1036 Wearer | some/all | Y | Y | some/all | Read-only | some/all |
| 1038 Medical Prof | Y | Y | N | some | Read-only | N |
| 1040 Nutritionist | some | Y | N | some | Read-only | N |
| 1042 Device Spec. | N | N | Y | Y | some | Y |
| 1044 App. S/W | some | some | some | some | N | some |

FIGURE 10

DATA PERMISSION MANAGEMENT FOR WEARABLE DEVICES

BACKGROUND

Unless otherwise indicated herein, the materials described in this section are not prior art to the claims in this application and are not admitted to be prior art by inclusion in this section.

Computing systems such as personal computers, laptop computers, tablet computers, cellular phones, and countless types of Internet-capable devices are prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." For example, some wearable devices are wearable computing devices are wrist-mounted devices that can worn like a wrist watch.

When a wearable computing device communicates wirelessly, such as with a smartphone or other computing device, typically device-level communications security is utilized. That is, once a secure wireless communication link is established between the wearable computing device and another device, any application on either device can utilize the secure wireless communication link.

SUMMARY

In one aspect, a method is provided. A wearable computing device stores data that includes data about a wearer of the wearable computing device. The wearable computing device receives a request for a portion of the stored data. The wearable computing device determines a designated role associated with the request for the portion of the stored data. The wearable computing device determines one or more rules regarding access to the portion of the sensitive data based on the designated role. The wearable computing device determines a response to the request for the portion of the stored data by at least: determining whether the request is validated by at least applying the one or more rules to the request, and after determining that the request is validated, providing the requested portion of the stored data.

In another aspect, a wearable computing device is provided. The wearable computing device includes a processor and a non-transitory computer readable medium. The non-transitory computer readable medium is configured to store at least data and executable instructions. The executable instructions, when executed by the processor, cause the wearable computing device to perform functions including: storing data in the non-transitory computer readable medium, where the stored data includes data about a wearer of the wearable computing device; receiving a request for a portion of the stored data; determining a designated role associated with the request for the portion of the stored data; determining one or more rules regarding access to the portion of the stored data based on the designated role; and determining a response to the request for the portion of the stored data by at least: determining whether the request is validated by at least applying the one or more rules to the request, and after determining that the request is validated, providing the requested portion of the stored data from the non-transitory computer readable medium.

In another aspect, a non-transitory computer readable medium is provided. The non-transitory computer readable medium is configured to store at least executable instructions. The executable instructions, when executed by a processor of a wearable computing device, cause the wearable computing device to perform functions including: storing data that includes data about a wearer of the wearable computing device; receiving a request for a portion of the stored data; determining a designated role associated with the request for the portion of the stored data; determining one or more rules regarding access to the portion of the sensitive data based on the designated role; and determining a response to the request for the portion of the stored data by at least: determining whether the request is validated by at least applying the one or more rules to the request, and after determining that the request is validated, providing the requested portion of the stored data.

In another aspect, a wearable computing device is provided. The wearable computing device comprises: means for storing data, the stored data including data about a wearer of the wearable computing device; means for receiving a request for a portion of the stored data; means for determining a designated role associated with the request for the portion of the stored data; means for determining one or more rules regarding access to the portion of the stored data based on the designated role; and means for determining a response to the request for the portion of the stored data by at least: determining whether the request is validated by at least applying the one or more rules to the request, and after determining that the request is validated, providing the requested portion of the sensitive data.

BRIEF DESCRIPTION OF THE DRAWINGS

FIG. 10 depicts example wearable device data and example wearable device roles.

DETAILED DESCRIPTION

Figure 1:
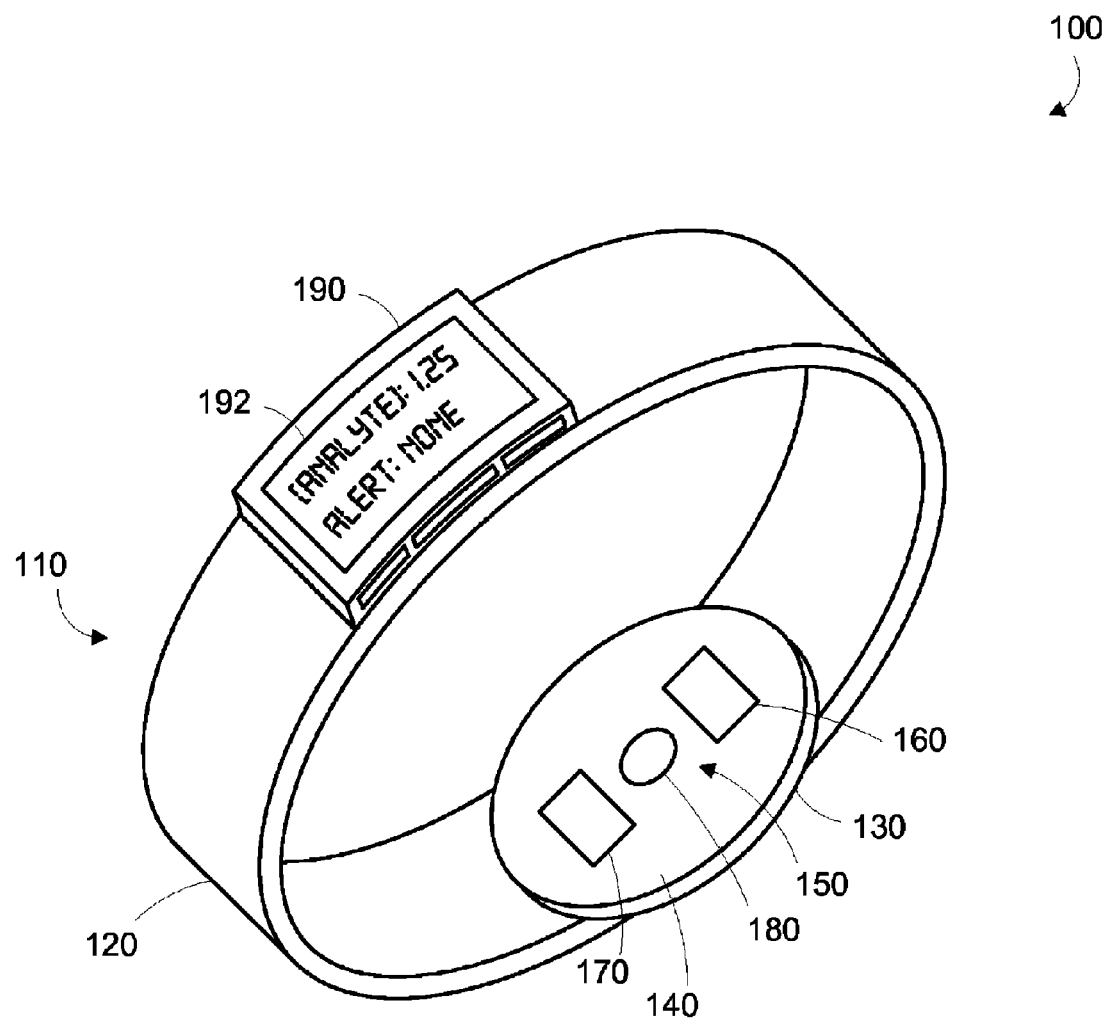
FIG. 1 is a perspective view of an example wearable device.

Permission Schemes and Data Sharing for Wearable Devices

An example wearable device is a wearable computing device that automatically detects, measures, and possibly stores data about a wearer wearing a device, where the data can include physiological and environmental parameters. The physiological parameters could include any parameters that may relate to the health of the wearer and the environmental parameters may relate to an environment about the wearer. To measure the physiological parameters, the wearable device can include sensors for measuring blood pressure, pulse rate, skin temperature, and/or one or more analytes in blood circulating in subsurface vasculature proximate to the wearable device. For example, the one or more analytes can include enzymes, hormones, proteins, cells or other molecules. In some cases, the wearable device can include sensors to measure environmental parameters related to the wearer, such as location, temperature, humidity, wind speed/direction, time of day, and illumination parameters.

The wearable device can include a mount that is configured to mount the device to a specific surface of the person's body, more particularly, to a body location where subsurface vasculature is readily observable. For example, the wearable device can include a wristband for mounting the wearable device on the wrist. In this position, the wearable device may be only about 2-4 millimeters away from the midpoint of an artery, capillary or vein in the wrist. In other cases, the wearable device can be mounted on/near other body locations.

The wearable device can further include memory for storing data, such as but not limited to the physiological parameters and/or results of the data analysis, and a communication interface for transmitting at least stored data to medical personnel and/or receiving instructions or recommendations based on those results. In some examples, the communication interface is a wireless communication interface. The communication interface may also include a universal serial bus (USB) interface, a secure digital (SD) card interface, a wired interface, or any other appropriate interface for communicating data from the device to a server. The term "server" may include any system or device that responds to requests across a computer network to provide, or helps to provide, a network service, and may include servers run on dedicated computers, mobile devices, and those operated in a cloud computing network.

Some or all of the data sharable by the wearable device can be considered as sensitive data to the wearer. Sensitive data can be data including, but not limited to, the above-mentioned physiological parameters, location data, device status data, electronic messages, and/or wearer-generated data (e.g., notes, voice recordings, documents). Non-sensitive data can be any data not designated as sensitive data. In some embodiments, data stored on a wearable device can be designated as sensitive or non-sensitive data by the wearer or other entity. In other embodiments, data can be determined to be sensitive or non-sensitive based on context. As an example, a network address may be non-sensitive data during a communications session but may be sensitive data at other times; for example, a network address obtained outside of a communication session that reveals a network location of a user and, by extension, a physical location related to the user. Many other examples of sensitive and non-sensitive data are possible as well.

Sensitive data, and perhaps non-sensitive data, can be communicated using secure communication links to other devices, such as associated computing devices and servers. Example associated computing devices include but are not limited to, smart phones, laptop computers, desktop computers, and tablet computers. The associated computing devices can provide functionality that may be difficult or impossible for the wearable devices, such as providing additional computing power, storage, communications interfaces, and/or user interfaces.

In some contexts, finer grained security for wearable-device data can be utilized. Security of data can be organized based on a role of an entity accessing, or attempting to access, data on the wearable device. For example, a role of "wearer" can access most, if not all, of the data on the wearable device, especially if the wearer owns or otherwise controls the wearable device. In other situations, the wearer can wear, but not own the wearable device—such as a wearable device worn as a condition for employment or if the wearer is borrowing the wearable device. Another example role of "manager" can be used to have access to most, if not all data, and the wearer role can access a different subset of data than the manager role.

Other entities may be able to access the wearable-device data for various reasons, and so be assigned various roles. As an example, a medical professional, such as a medical doctor or nurse, may have access to physiological data on the wearable device, but not be granted access to application data, such as information downloaded to the wearable device by the wearer. In this example, a "medical professional" role can be granted access to most, if not all, physiological data, but little or no access to application data. A technician who administers and/or repairs wearable devices may have an "administrator" role to access to all data to permit administration and repair of the wearable device. A person related to the wearer, such as a spouse, child, or friend of the wearer, may be assigned a "borrower" role so the related person can borrow the wearable device, but not have access to sensitive data associated with the wearer; e.g., the wearer's physiological data. Further, the wearer may not have access to physiological data of the borrower.

The designation of data as sensitive or not-sensitive can be specified as well. For example, networking data used to allow the wearable device to connect with other device may be generally considered as non-sensitive. Application data associated with the wearer, such as information downloaded to the wearable device, may be considered sensitive or non-sensitive depending on context. Rules on designation of data as sensitive or non-sensitive can specify such contexts where data is sensitive (or non-sensitive).

Access to data on a wearable device can be controlled by specification of roles controlling access of data and the designation of data as sensitive or not-sensitive. The control of wearable device data access can enable a wide range of acceptable or validated data accesses—from little or no access related to some roles, to complete access for other roles. Further, the concepts of wearer and device manager can be separated, enabling management of a wearable device by someone other than the owner. As wearable devices become more complicated and/or as wearable devices are owned by others than wearers, the management function of the wearable device can become decoupled from the wearing function. Further, allowing access to role-specific portions of wearable device data can enable a wider variety of applications to utilize the wearable device.

Example Wearable Devices

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house the data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. At least one of the detectors 160 is configured to non-invasively measure one or more analytes in blood circulating in subsurface vasculature proximate to the wearable device. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

In an example embodiment, the wearable device obtains at least some of the health-related information by detecting the binding of a clinically-relevant analyte to functionalized particles, for example, microparticles or nanoparticles introduced into a lumen of the subsurface vasculature. The term "binding" is understood in its broadest sense to also include a detectable interaction between the clinically relevant analyte and the functionalized particles. The particles can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. Those of skill in the art will understand a "particle" in its broadest sense and that it may take the form of any fabricated material, a molecule, cryptophane, a virus, a phage, etc. Further, a particle may be of any shape, for example, spheres, rods, non-symmetrical shapes, etc.

In some examples, the particles may be magnetic and can be formed from a paramagnetic, super-paramagnetic or ferromagnetic material or any other material that responds to a magnetic field. Alternatively, the particles may also be made of non-magnetic materials such as polystyrene.

The particles, or a group of several particles in a complex, may be functionalized with a receptor that has a specific affinity to bind to or interact with a clinically relevant analyte. The receptor may be inherent to the particle itself. For example, the particle itself may be a virus or a phage with an inherent affinity for certain analytes. Additionally or alternatively, the particles can be functionalized by covalently attaching a receptor that specifically binds or otherwise recognizes a particular clinically-relevant analyte. The functionalized receptor can be an antibody, peptide, nucleic acid, phage, bacteria, virus, or any other molecule with a defined affinity for a target analyte. Other compounds or molecules, such as fluorophores or autofluorescent or luminescent markers, which may assist in interrogating the particles in vivo, may also be attached to the particles.

The functionalized particles can be introduced into the person's blood stream by injection, ingestion, inhalation, transdermally, or in some other manner. Where magnetic particles are used, the wearable device may include a magnet that can direct into the portion of subsurface vasculature a magnetic field that is sufficient to cause the functionalized magnetic particles to collect in a lumen of that portion of subsurface vasculature. However, measurements may be taken without localized "collection" of the functionalized particles. The wearable device may be configured to activate the magnetic periodically, such as at certain times of every day (e.g., every hour).

In some examples, the data collection system 150 further includes a signal source 170 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the functionalized particles. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the particles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the functionalized particles include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 100 may not include a signal source 170. For example, the functionalized particles include an autofluorescent or luminescent marker, such as a fluorophore, that will automatically emit a response signal indicative of the binding of the clinically-relevant analyte to the functionalized particles, without the need for an interrogating signal or other external stimulus. In some examples, the functionalized particles may include a chemoluminescent marker configured to produce a response signal in the form of fluorescence radiation produced in response to a chemical reaction initiated, at least in part, to the binding of the target analyte to the particle.

A collection magnet 180 may also be included in the data collection system 150. In such embodiments, the functionalized particles may also be made of or be functionalized with magnetic materials, such as ferromagnetic, paramagnetic, super-paramagnetic, or any other material that responds to a magnetic field. The collection magnet 180 is configured to direct a magnetic field into the portion of subsurface vasculature that is sufficient to cause functionalized magnetic particles to collect in a lumen of that portion of subsurface vasculature. The magnet may be an electromagnet that may be turned on during measurement periods and turned off when a measurement period is complete so as to allow the magnetic particles to disperse through the vasculature.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
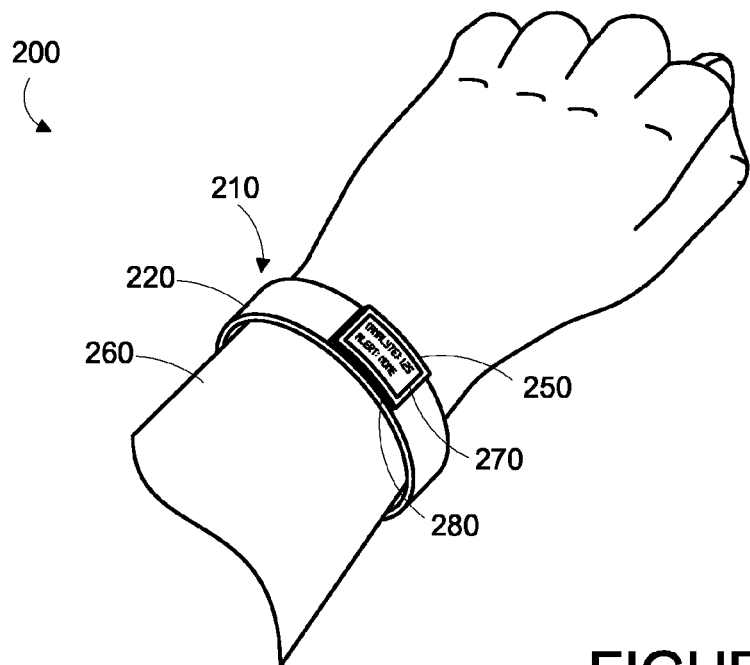
FIG. 2A is a perspective top view of an example wrist-mounted device, when mounted on a wearer's wrist.
Figure 2B:
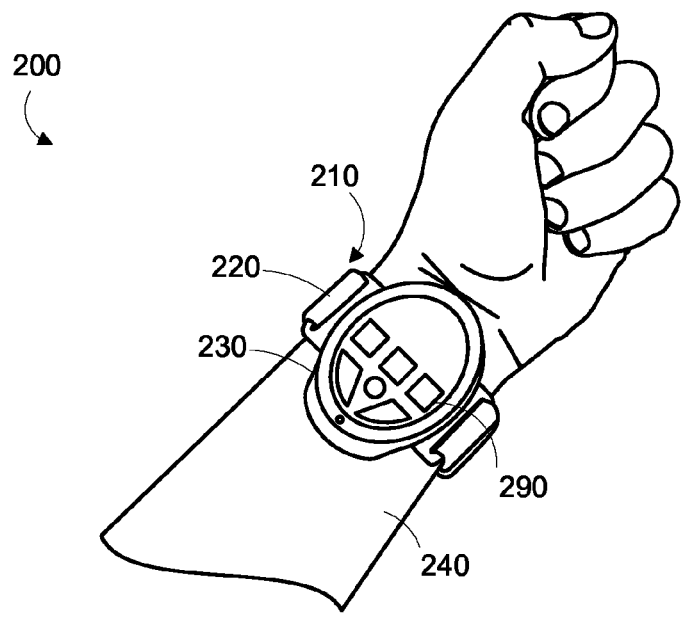
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 5B, and 6. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
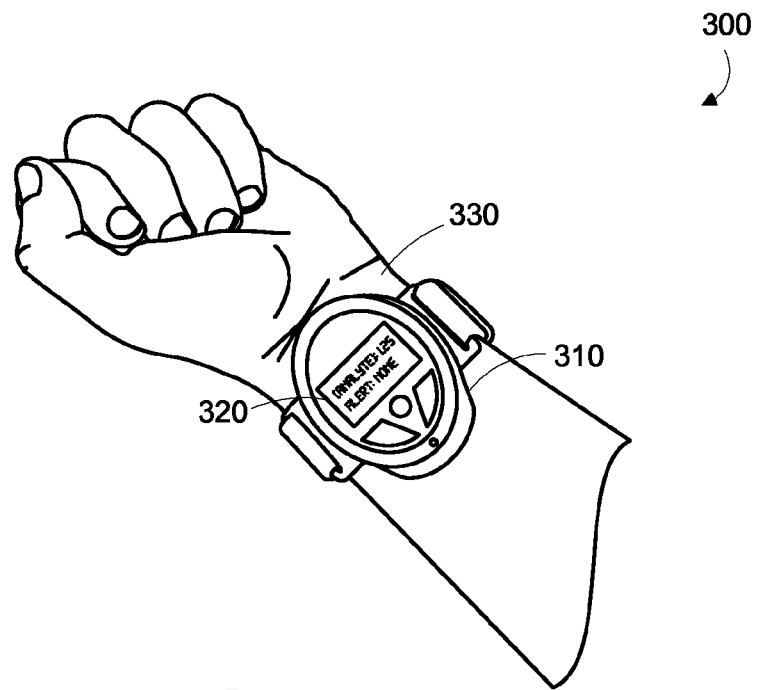
FIG. 3A is a perspective bottom view of an example wrist-mounted device, when mounted on a wearer's wrist.
Figure 3B:
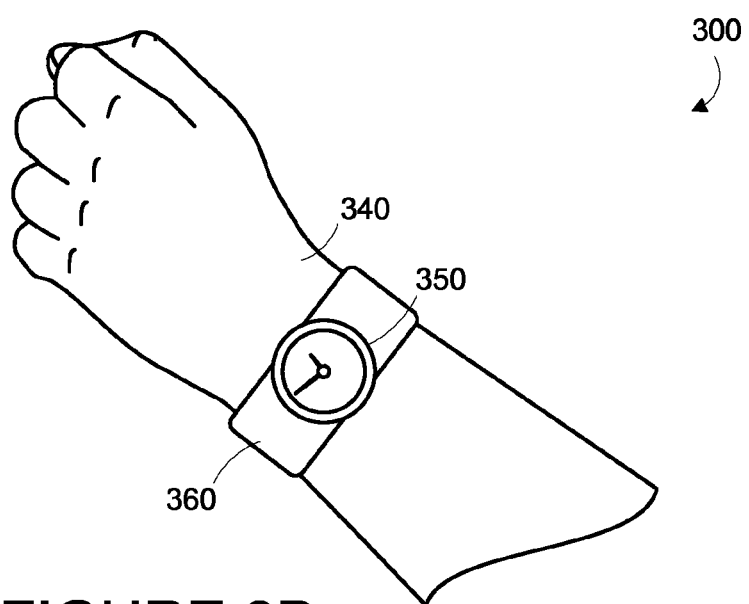
FIG. 3B is a perspective top view of an example wrist-mounted device shown in FIG. 3A, when mounted on a wearer's wrist.
Figure 3C:
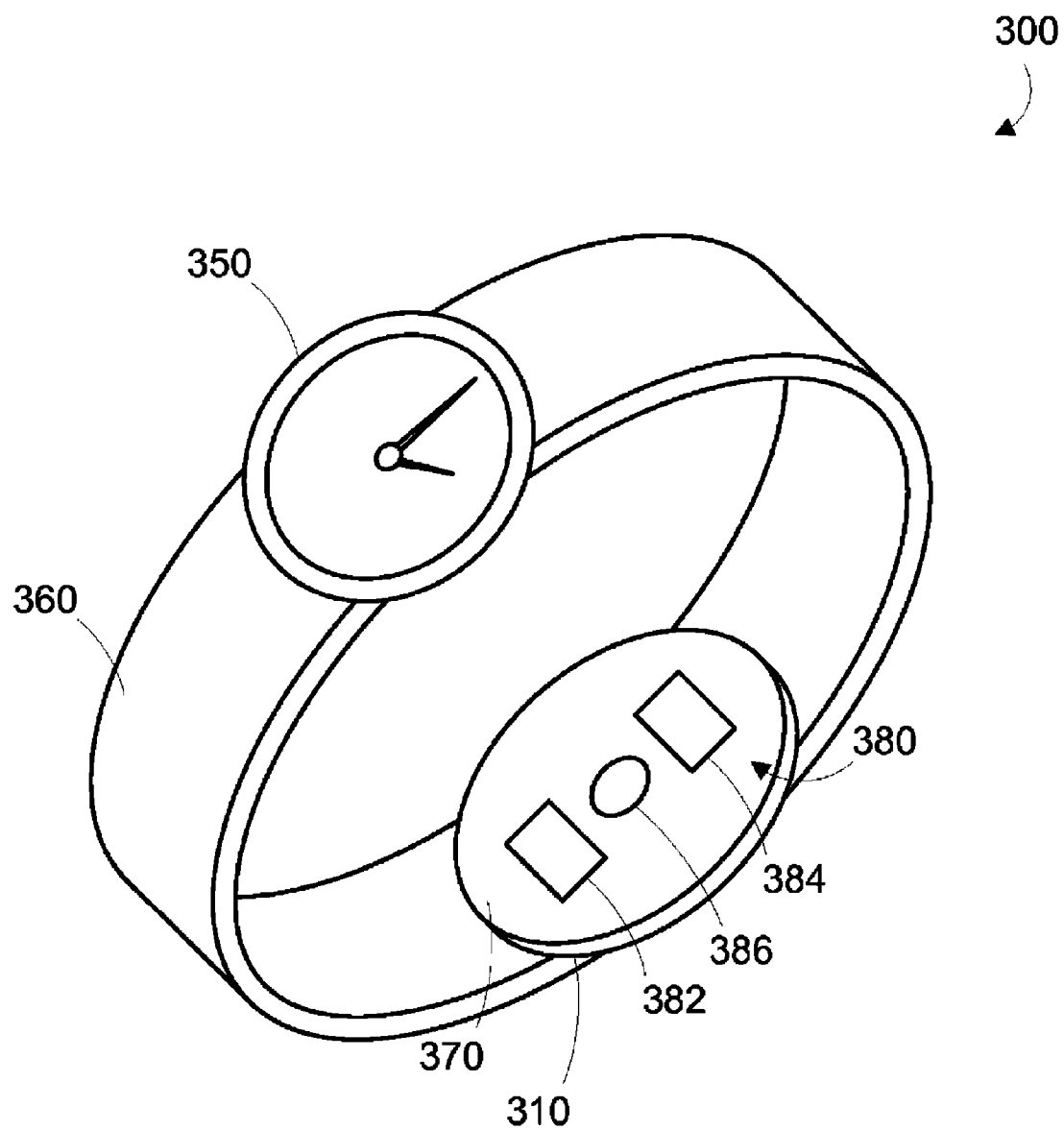
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382, a signal source 384 and a collection magnet 386. As described above, the signal source 384 and the collection magnet 386 may not be provided in all embodiments of the wearable device.

Figure 4A:
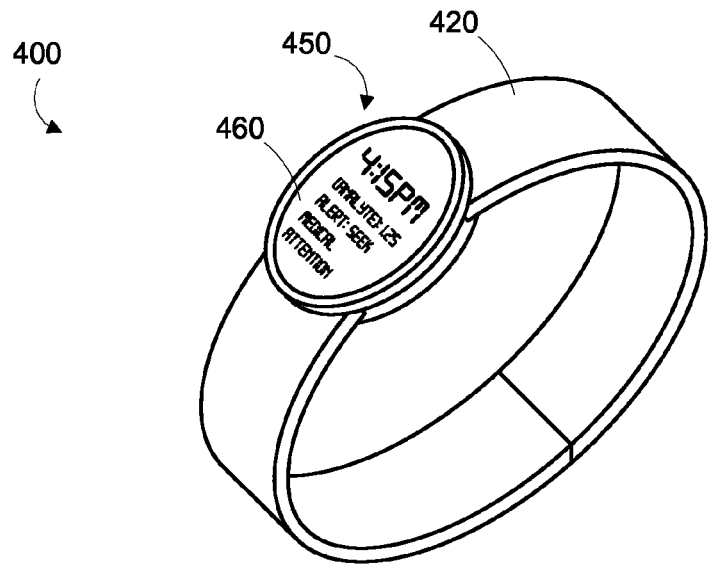
FIG. 4A is a perspective view of an example wrist-mounted device.
Figure 4B:
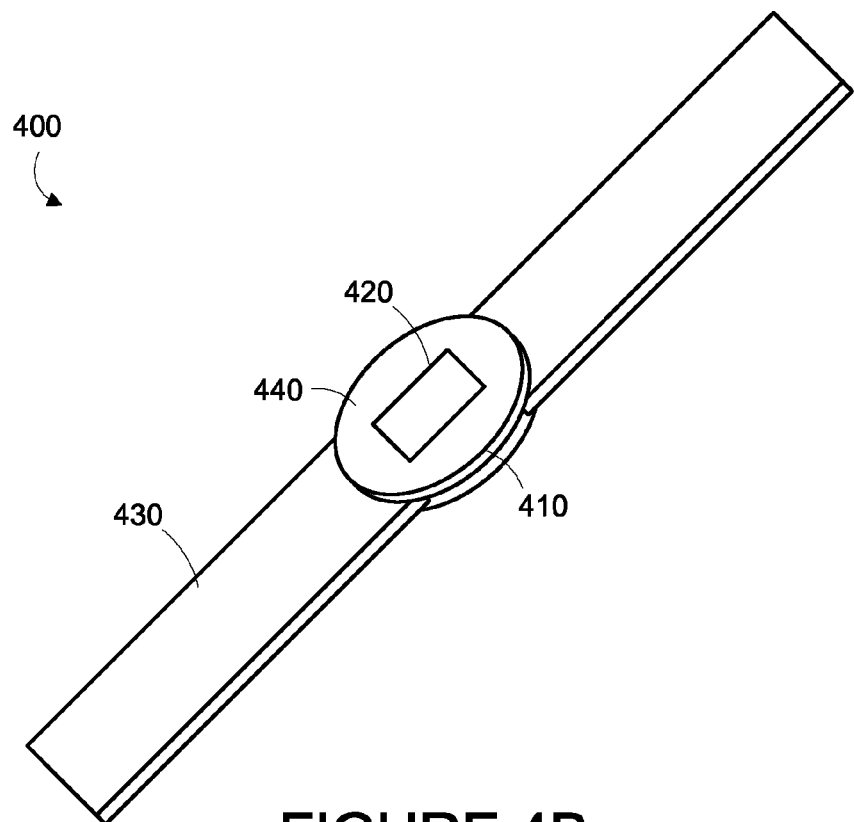
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
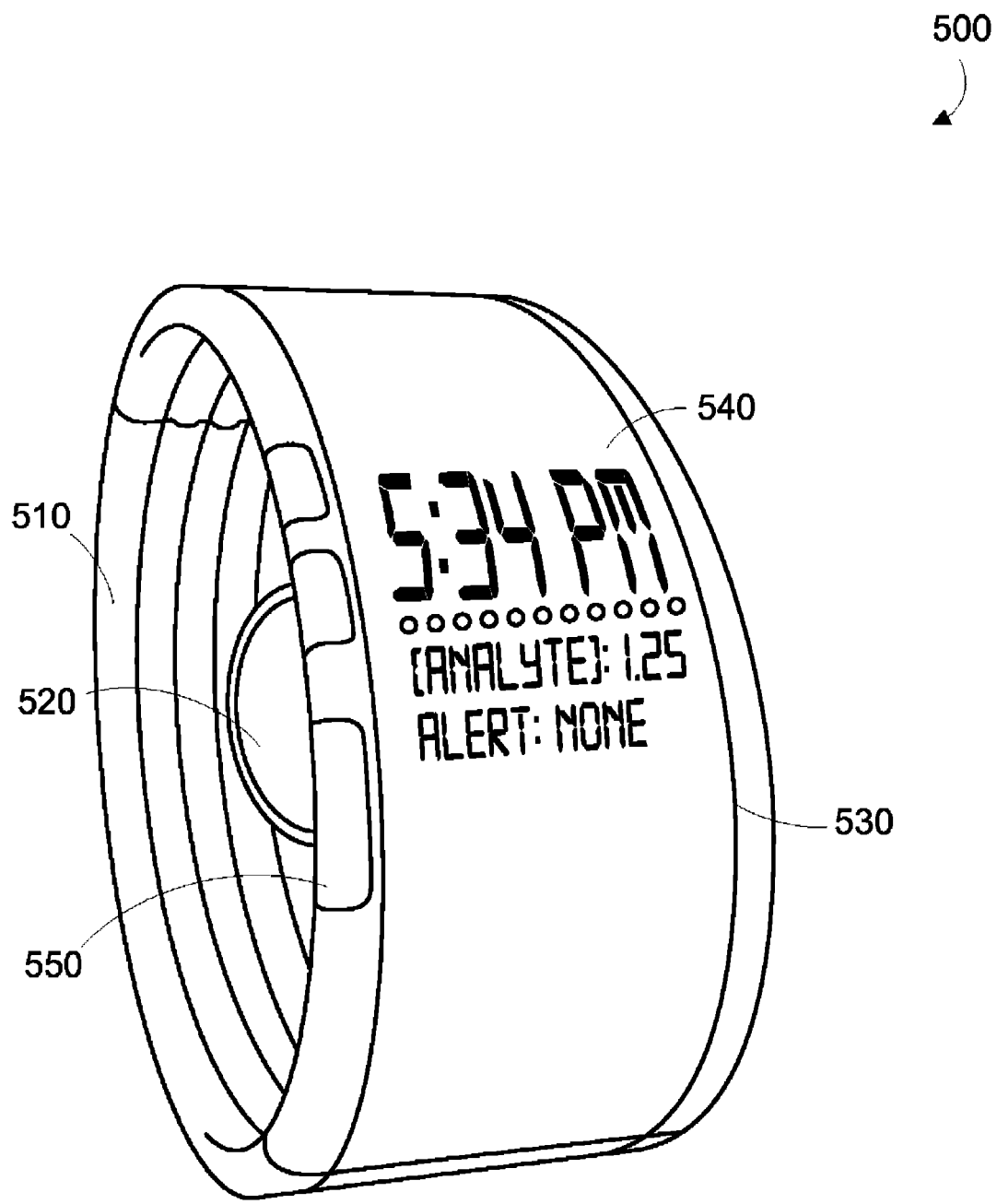
FIG. 5 is a perspective view of an example wrist-mounted device.
Figure 6:
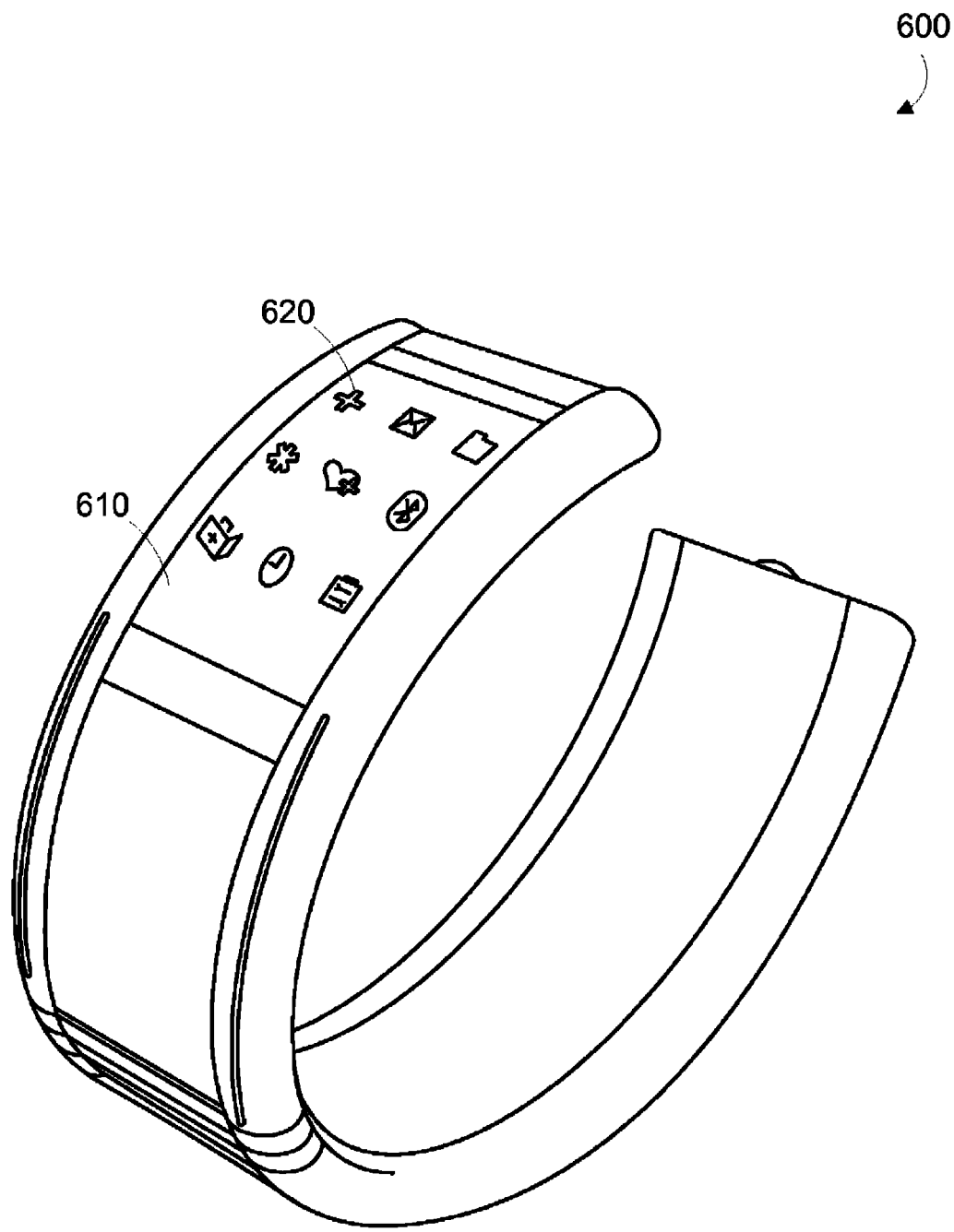
FIG. 6 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer. For example, as shown in FIG. 6, display 610 may be a touch-screen configured to display one or more virtual buttons 620 for accepting one or more inputs for controlling certain functions or aspects of the wearable device 600, or inputs of information by the user, such as current health state.

Figure 7A:
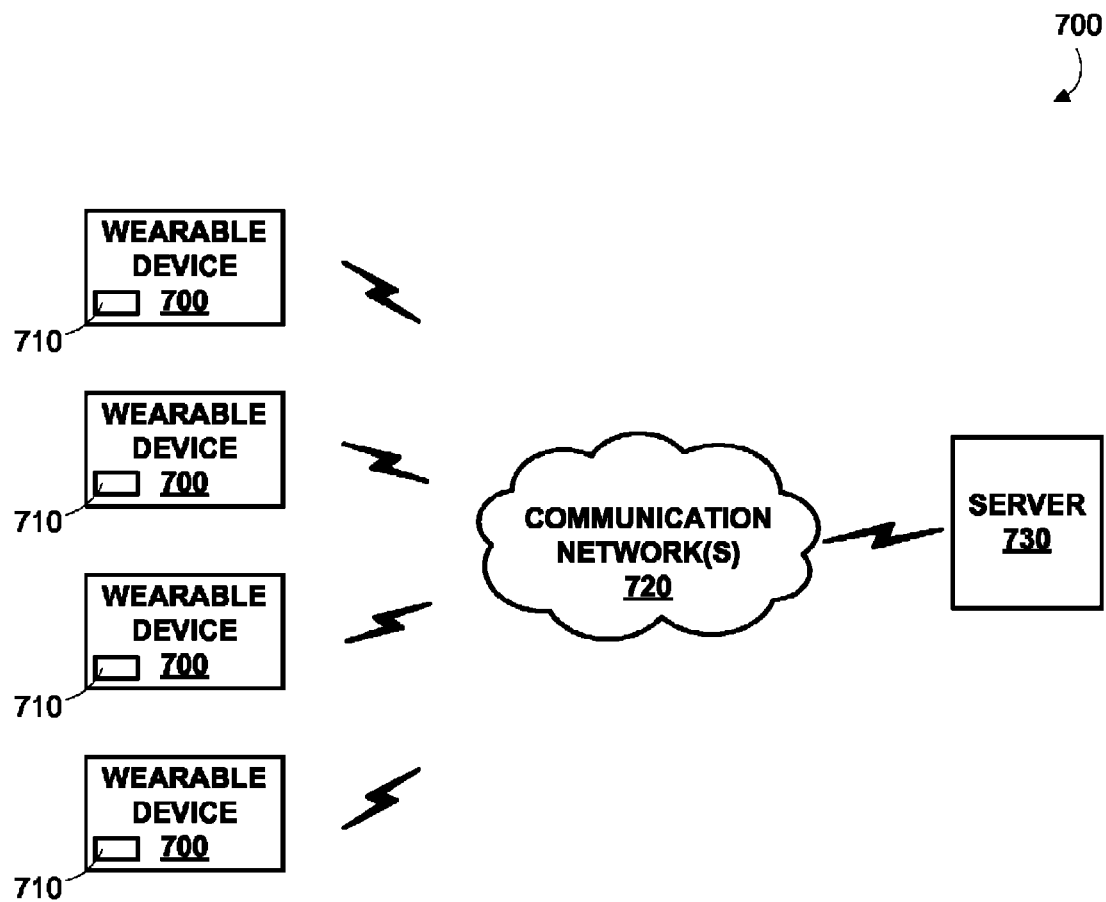
FIG. 7A is a block diagram of an example system that includes a plurality of wrist mounted devices in communication with a server.

FIG. 7A is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer.

In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 7B:
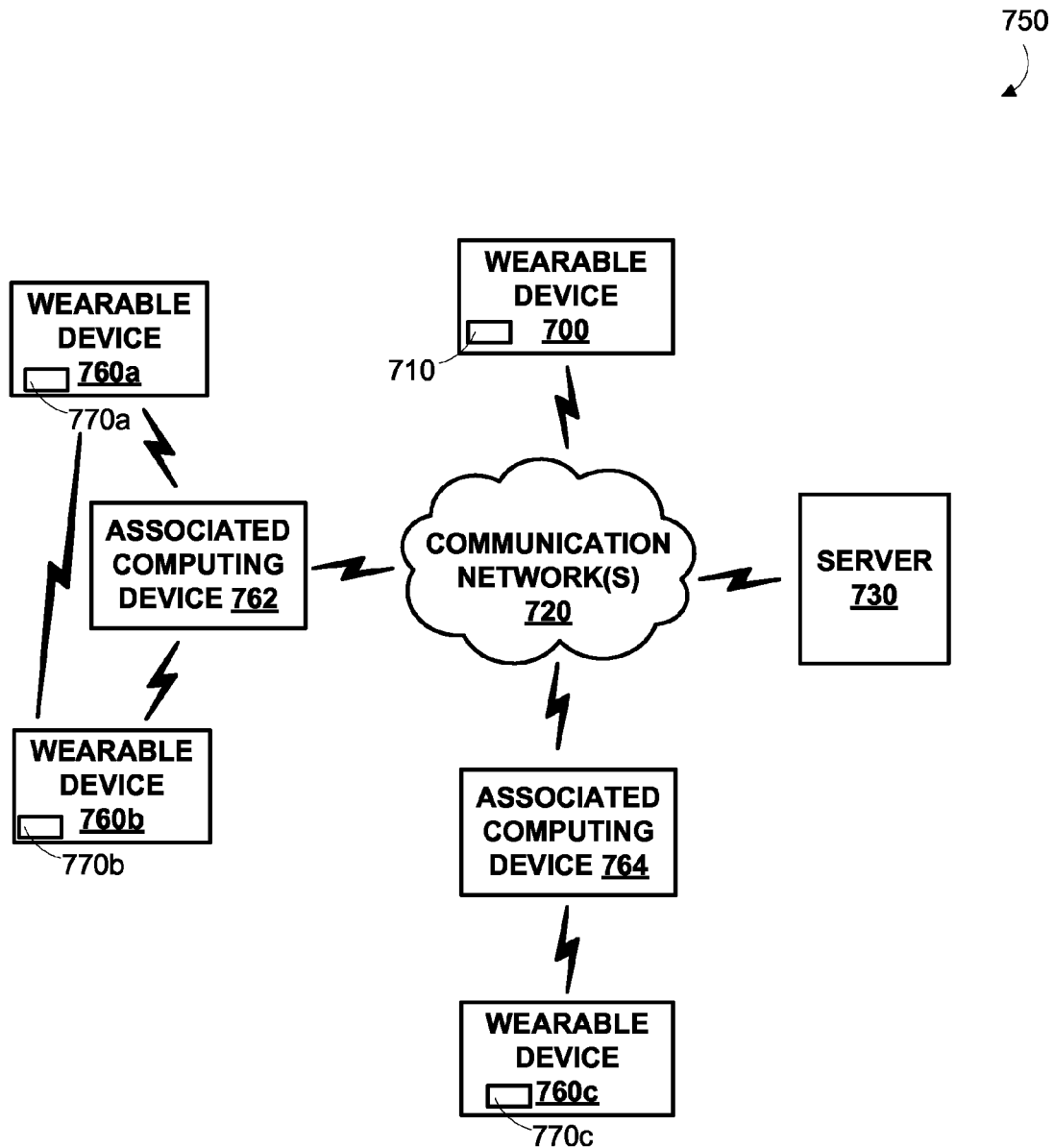
FIG. 7B is a block diagram of an example system that includes a plurality of wrist mounted devices and associated computing devices in communication with a server.

FIG. 7B is a simplified schematic of system 750 including one or more wearable devices 700, 760a, 760b, 760c, and associated computing devices 762, 764. As in FIG. 7A, wearable device 700 may be configured to transmit data via a communication interface 710a over one or more communication networks 720 to remote server 730. FIG. 7B shows wearable devices 760a, 760b may be configured to communicate data via respective communication interfaces 770a, 770b to associated computing device 762, and that wearable devices 760a, 760b may be configured to communicate directly to each other.

FIG. 7B also shows that wearable device 760c may be configured to communicate data via communication interface 770c to associated computing device 764. Each of associated computing devices 762, 764 may be configured to communicate data over one or more communication networks 720 to remote server 730. Associated computing devices 762, 764 can be computing devices, such as, but not limited to, smart phones, laptop computers, desktop computers, and tablet computers. As such, some or all of communication interfaces 770a, 770b. 770c may be configured for low-powered, short-range communications; for example, communications using a Bluetooth® protocol and/or a ZigBee® protocol.

Figure 8:
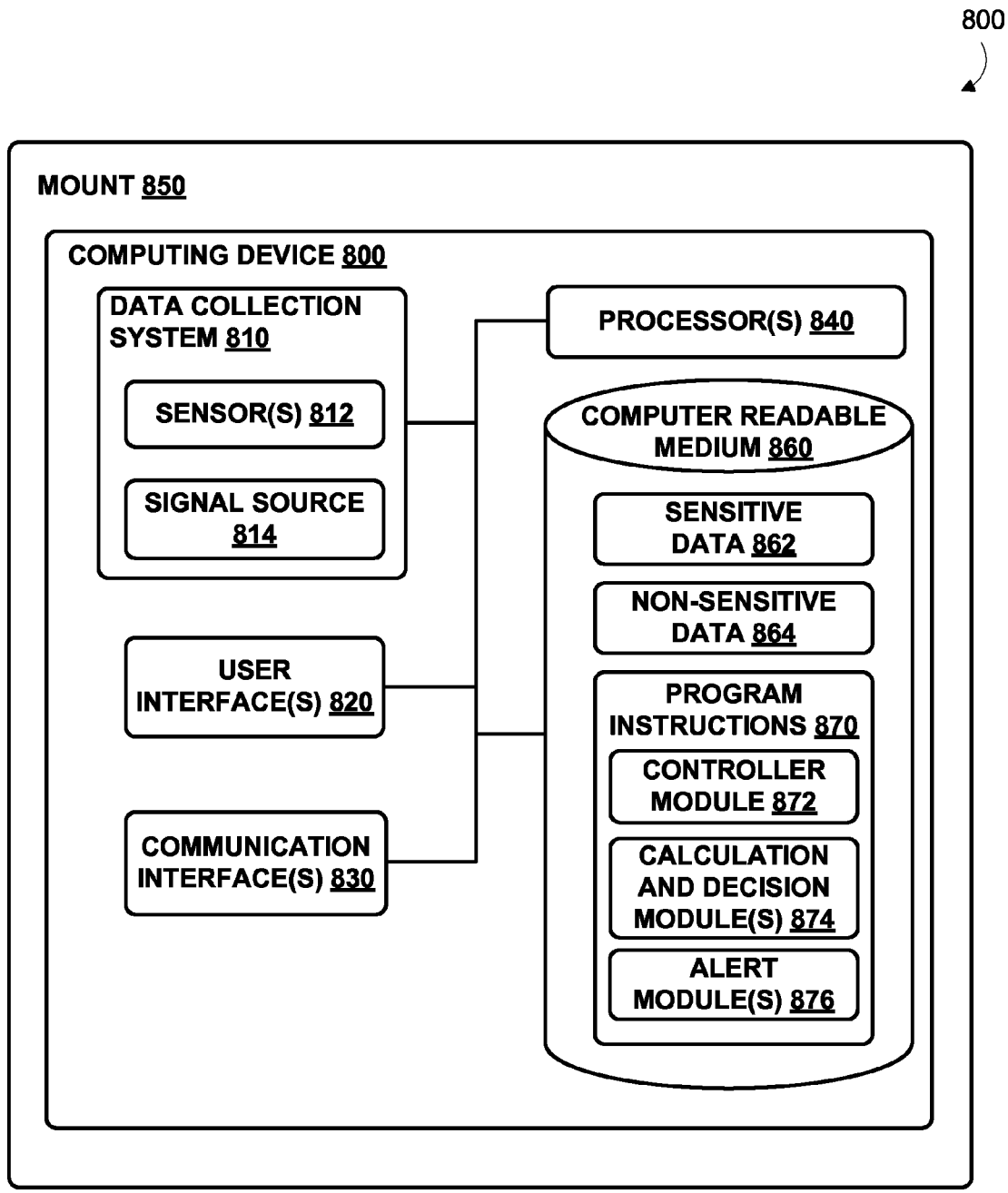
FIG. 8 is a functional block diagram of an example wearable device.

FIG. 8 is a simplified block diagram illustrating the components of a computing device 800, according to an example embodiment. Computing device 800 may be configured to carry out some or all of the herein-described functionality of wrist-mounted devices 200, 300, 400, 500, 600, shown in FIGS. 2A-B, 3A-3C, 4A-4B, 5 and 6, wearable devices 700, 760*a*, 760*b*, 760*c* shown in FIGS. 7A, 7B, and 10-14, server 730 shown in FIGS. 7A, 7B, 10, 13, and 14, and/or associated computing devices 762, 764 shown in FIGS. 7B, 10, 11, and 12. However, computing device 800 may also take other forms, such as, but not limited to, an ankle-mountable device, a waist-mountable device, a chest-mountable device, a head-mountable device, or an immobile computing device.

In particular, FIG. 8 shows an example of a computing device 800 having a data collection system 810, a user interface 820, communication platform 830 for transmitting data to a server, and processor(s) 840. The components of the computing device 800 may be disposed on a mount 850 for mounting the device to an external body surface or other surface.

Processor(s) 840 may be one or more general-purpose processors and/or special purpose processors (e.g., digital signal processors, application specific integrated circuits, graphics processing units, etc.). Processor(s) 840 can be configured to execute computer-readable program instructions 870 that are stored in the computer readable medium 860 and are executable to provide the functionality described herein, including but not limited to, the functionality of a wearable device, associated computing device, and/or server described herein. The computer readable medium 860 may further contain other data or information usable provide the functionality described herein, including but not limited to, the functionality of a wearable device, associated computing device, and/or server described herein. For example, as shown in FIG. 8, computer readable medium 860 can store sensitive data 862, such as physiological and/or other biological data obtained by computing device 800, and non-sensitive data 864, which can include data other than sensitive data 862.

In some embodiments, sensitive data 862 can be physically separated from non-sensitive data 864; e.g., sensitive data 862 can be stored in physical component(s) of computer readable medium that differ(s) from physical component(s) of computer readable medium 860 storing non-sensitive data 864. In other embodiments, sensitive data 862 can be logically separated from non-sensitive data 864. For example, both sensitive data 862 and non-sensitive data 864 can be stored in a database or other data storage structure. But sensitive data 862 can be accessed differently than non-sensitive data 864; e.g., based on information in a database query, access right(s) granted to sensitive data 862, and/or other information.

Some data can be sensitive data in some contexts and non-sensitive data in otherwise; e.g., location data for computing device 800 can be non-sensitive when provided to an entity CLE co-located or nearly col-located with computing device 800, such as an associated computing device discussed at least in the context of FIG. 7B, and can be sensitive otherwise. In some contexts, the data can be considered to be non-sensitive to entity CLE, as CLE could provide its location as an estimate of location data from computing device 800. However, in other contexts, such as computing device 800 not authorizing transmission of location (or other) data, then the location (or other) data can be considered to be sensitive. Many other examples of determining sensitive and/or non-sensitive data are possible as well.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes sensor(s) 812 and, in some embodiments, a signal source 814. Signal source 814 may generate an interrogation signal, timing signal, and/or other signal that will produce a responsive signal that can be detected by one or more of sensor(s) 812.

Sensor(s) 812 may include any sensor and/or detector capable of detecting at least one physiological parameter, which could include any parameters that may relate to the health of the person wearing the wearable device. For example, sensor(s) 812 could include one or more detectors and/or sensors configured to measure physiological data, such as blood pressure, pulse rate, skin temperature, etc. At least one of the detectors 812 is configured to non-invasively measure one or more analytes in blood circulating in subsurface vasculature proximate to the wearable device. In some examples, detector 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some embodiments, sensor(s) 812 may include one or more sensors and/or detectors configured to measure conditions in an environment about computing device 800 and provide data about that environment. The data can include, but is not limited to: data about computing device 800, location data about computing device 800, velocity (speed, direction) data about computing device 800, acceleration data about computing device 800, and other data about the environment for computing device 800. Examples of sensor(s) 800 configured to measure conditions in an environment include, but are not limited to, power sensor(s), battery sensor(s), movement sensor(s), GPS sensor(s), location sensors(s), gyroscope(s), accelerometer(s), magnetometer(s), camera(s), light sensor(s), infrared sensor(s), and microphone(s).

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, sensor(s) 812 and signal source 814. For example, the controller 872 may activate signal source 814 and/or sensor(s) 812 during each of the pre-set measurement periods. The controller module 872 can also include instructions for operating a user interface 820. For example, controller module 872 may include instructions for displaying data collected by the data collection system 810 and analyzed by the calculation and decision module 874, or for displaying one or more alerts generated by the alert module 876. Further, controller module 872 may include instructions to execute certain functions based on inputs accepted by the user interface 820, such as inputs accepted by one or more buttons disposed on the user interface.

User interface 820 may be operable to send data to and/or receive data from external user input/output devices. For example, user interface 820 can be configured to send and/or receive data to and/or from user input devices such as a keyboard, a keypad, a touch screen, a computer mouse, a track ball, a joystick, a camera, a voice recognition module, and/or other similar devices. User interface 820 can also be configured to provide output to user display devices, such as one or more cathode ray tubes (CRT), liquid crystal displays (LCDs), light emitting diodes (LEDs), displays using digital light processing (DLP) technology, printers, light bulbs, and/or other similar devices, either now known or later developed. User interface 820 can also be configured to generate audible output(s), such as a speaker, speaker jack, audio output port, audio output device, earphones, and/or other similar devices. In some embodiments, user interface 820 can be configured to generate haptic output(s), such as vibrations and/or other outputs detectable by touch and/or physical contact with computing device 800.

Communication interface 830 may also be operated by instructions within the controller module 872, such as instructions for sending and/or receiving information via a wireless interface, which may be disposed on or in computing device 800. A wireless interface can include one or more antennas, wireless transmitters, wireless receivers, and/or wireless transceivers, such as a Bluetooth transceiver, a Zigbee transceiver, a Wi-Fi transceiver, a WiMAX transceiver, and/or other similar type of wireless transceiver configurable to communicate via a wireless network. The communication interface 830 can optionally include one or more oscillators, mixers, frequency injectors, etc. to modulate and/or demodulate information on a carrier frequency to be transmitted and/or received by the wireless interface. In some examples, the wearable device 800 is configured to indicate an output from the processor by modulating an impedance of the antenna in a manner that is perceivable by a remote server or other remote computing device.

In some embodiments, communication interface 830 can include a wired interface. The wired interface can include one or more wireline transmitters, receivers, and/or transceivers, such as a Universal Serial Bus (USB) transceiver, an Ethernet transceiver, and/or similar transceiver configurable to communicate via a twisted pair wire, a coaxial cable, a fiber-optic link, or a similar physical connection to a wired network.

Calculation and decision module 874 may include instructions for receiving data from the data collection system 810 in the form of a responsive signal and for analyzing the data. In particular, the calculation and decision module 874 may include instructions for determining a concentration of a clinically-relevant analyte based on the response signal detected by the detector at that measurement time and determining whether a medical condition is indicated based on at least the corresponding concentration of the clinically-relevant analyte. These determinations could be made at preset measurement times, which could be set to any period, such as at or about one hour apart.

The program instructions of the calculation and decision module 874 may, in some examples, be stored in a computer-readable medium and executed by a processor located external to the wearable device; e.g., associated computing device 760, 762 and/or server 730 as shown in FIGS. 7A and 7B above. For example, the wearable device could be configured to collect certain data regarding physiological parameters from the wearer and then transmit the data to a remote server, which may include a mobile device, a personal computer, one or more computing devices in a computing network, or any other remote system, for further processing.

Example Methods of Operation

Figure 9:
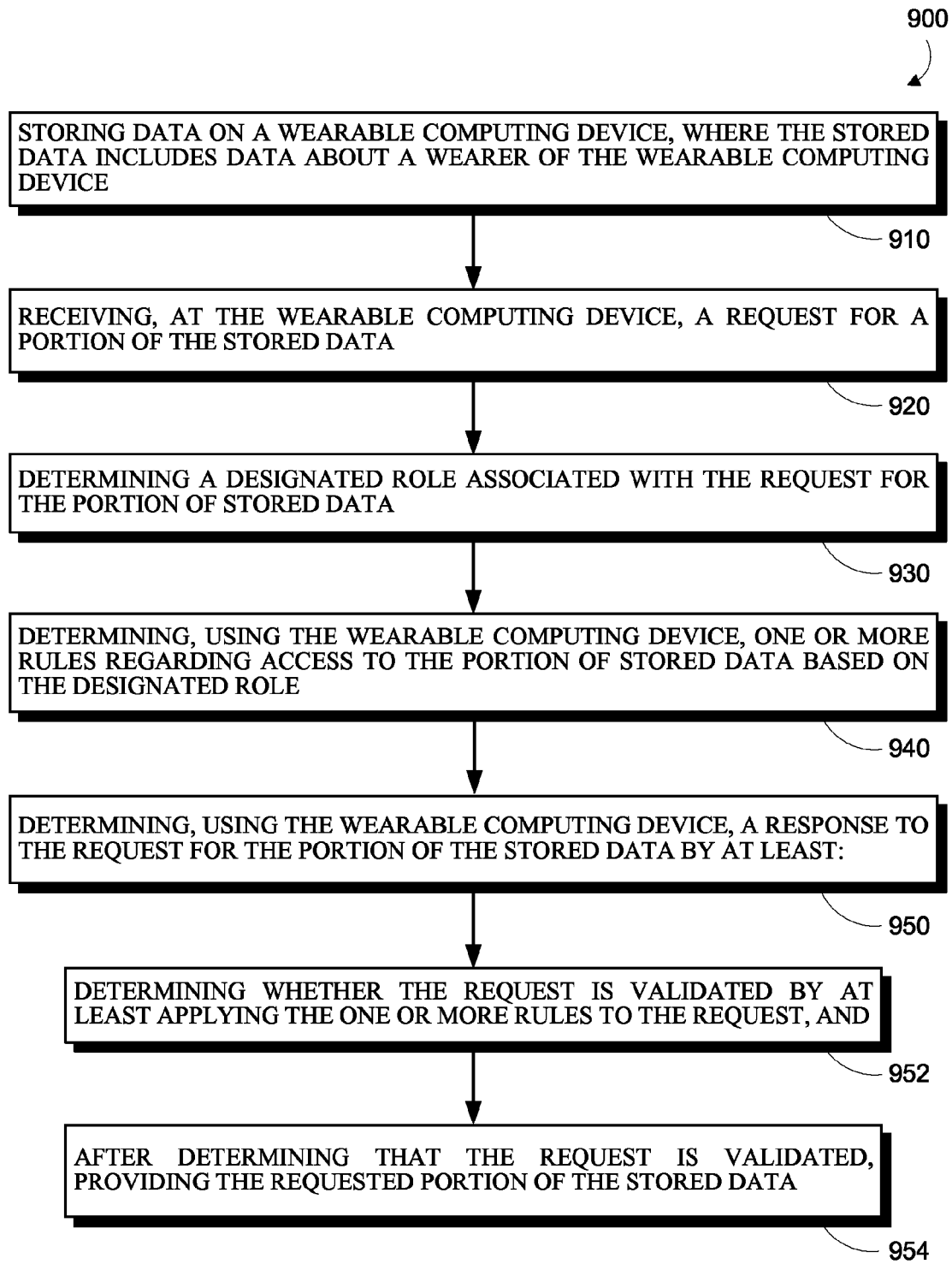
FIG. 9 is a flowchart of an example method.

FIG. 9 is a flowchart of a method 900 communicating data from a wearable computing device. Example wearable computing devices include, but are not limited to, wearable devices 100, 200, 300, 400, 500, 600, 700, 760a-760c, and 800 discussed herein with respect to FIGS. 1-8 and 10-15.

Method 900 can begin at block 910, where a wearable computing device can store data. The stored data can include data about a wearer of the wearable computing device, such as discussed herein with respect to FIGS. 1-8 and 10-15. In some embodiments, the stored data can include sensitive data, where the sensitive data can include data about physiological parameters of the wearer of the wearable computing device, such as discussed herein with respect to FIGS. 10 and 12.

Figure 12:
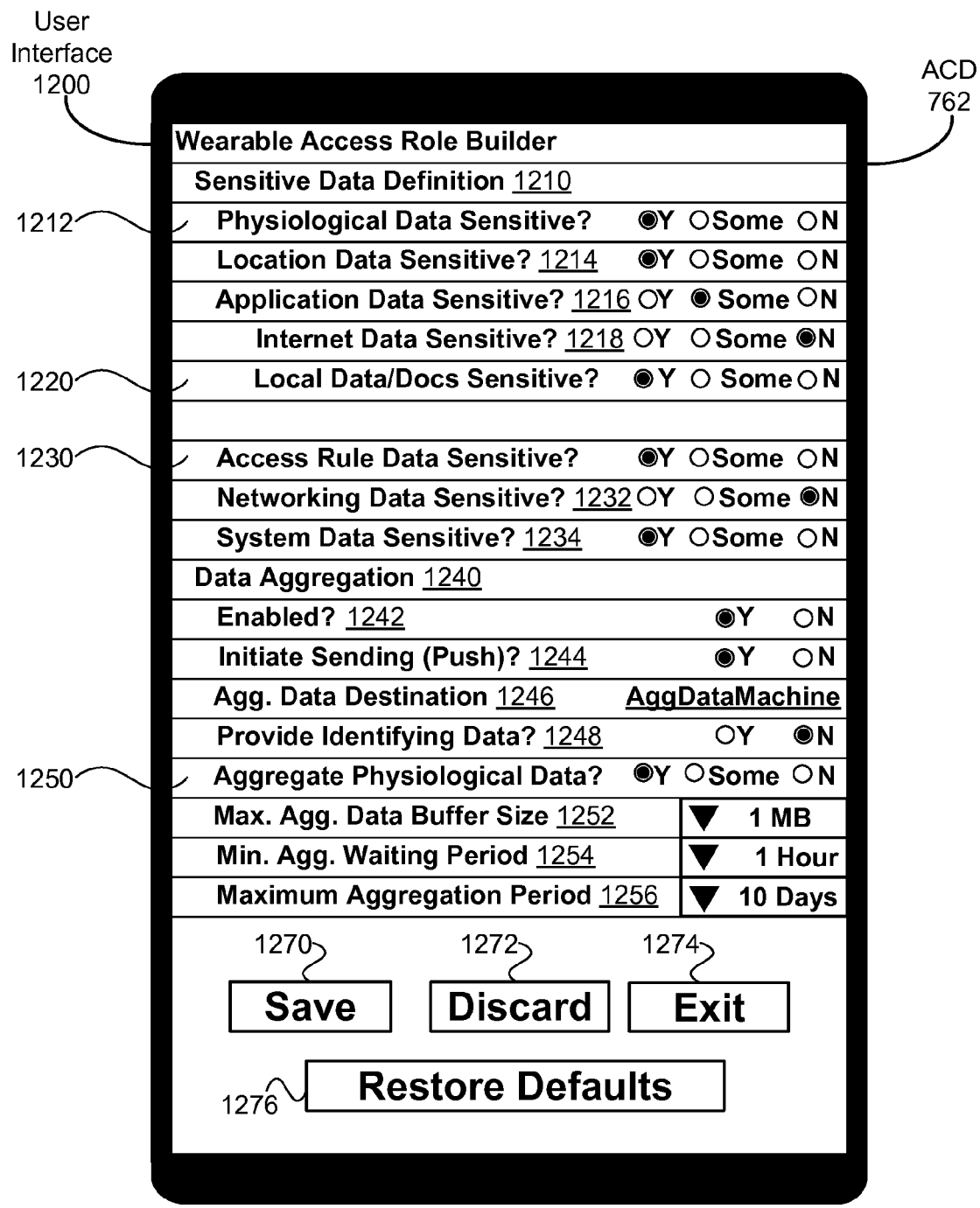
FIG. 12 depicts an example user interface for defining sensitive data.

In particular embodiments, the sensitive data can be defined based on one or more designations regarding sensitive data, such as discussed herein with respect to FIG. 12. In some of these particular embodiments, at least one designation of the one or more designations regarding sensitive data can relate to a time for accessing sensitive data, such as discussed herein with respect to FIG. 12. In other of these particular embodiments, at least one designation of the one or more designations regarding sensitive data can relate to a time when sensitive data was generated, such as discussed herein with respect to FIG. 12. In still other embodiments, the data about the wearer can include data about a context of the wearer and/or data about an environment for the wearer.

Figure 13:
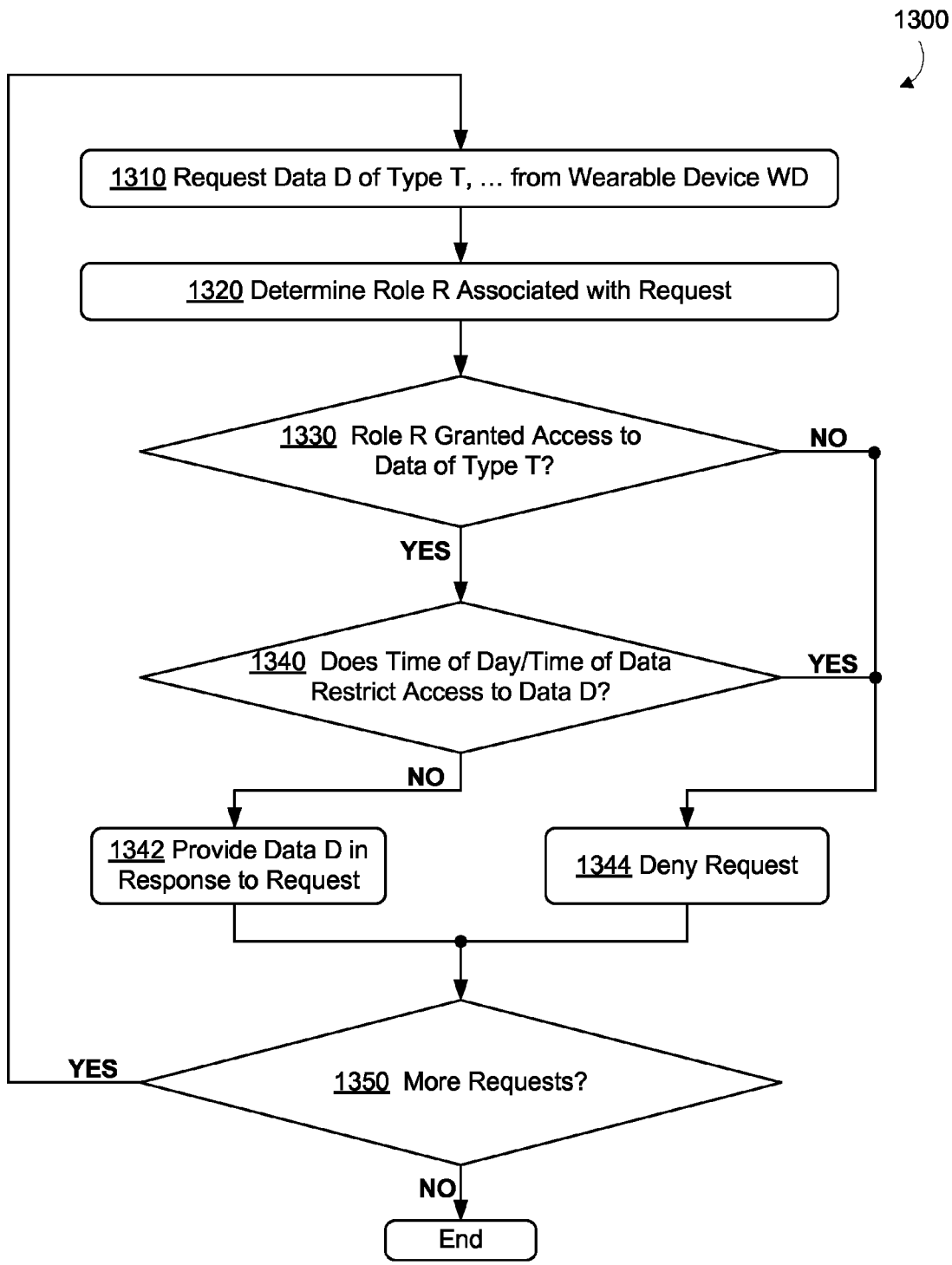
FIG. 13 is a flow chart for an example method for providing data based on roles.
Figure 14:
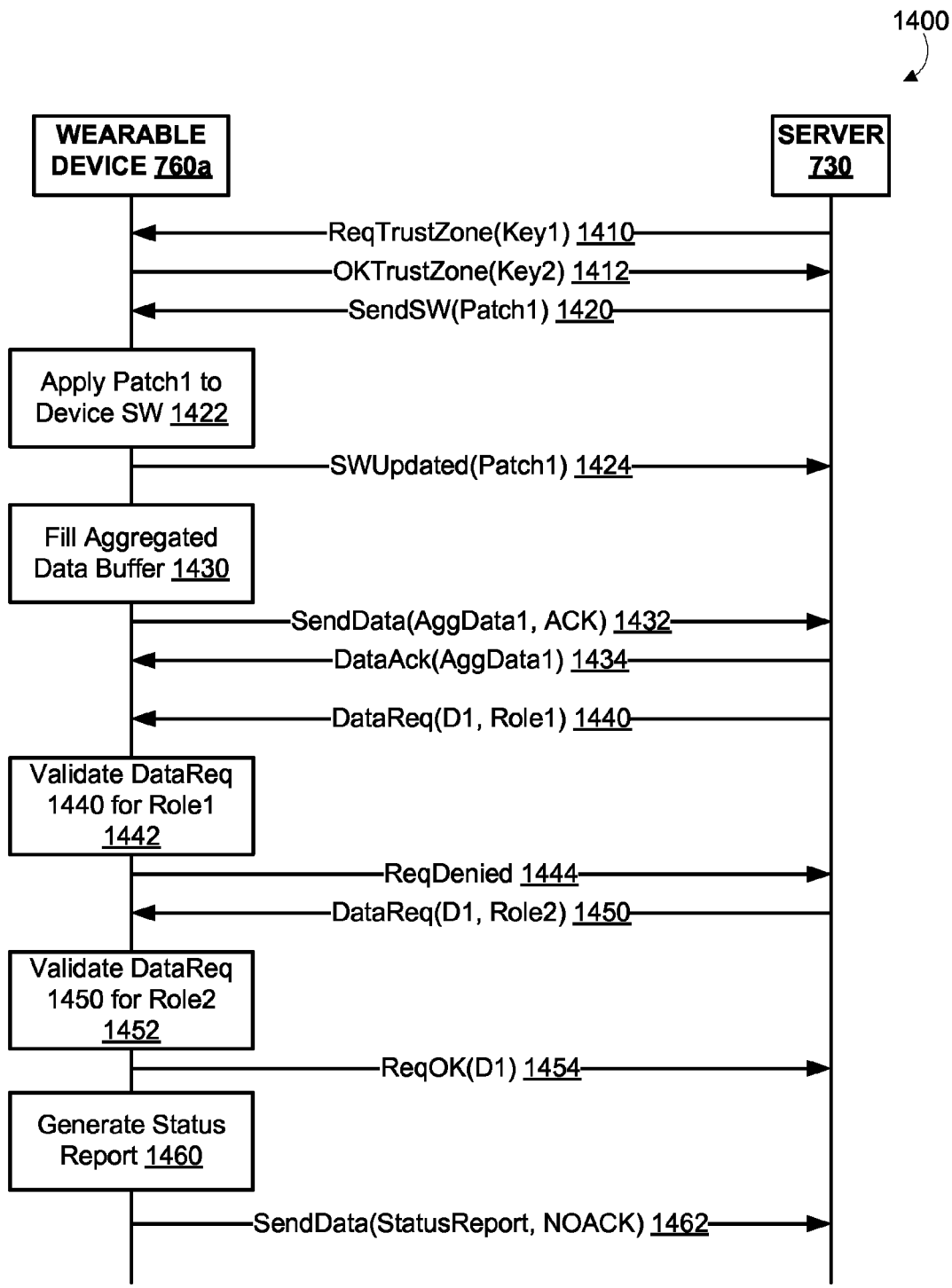
FIG. 14 depicts an example scenario with communication between a wearable device and a server.
Figure 15:
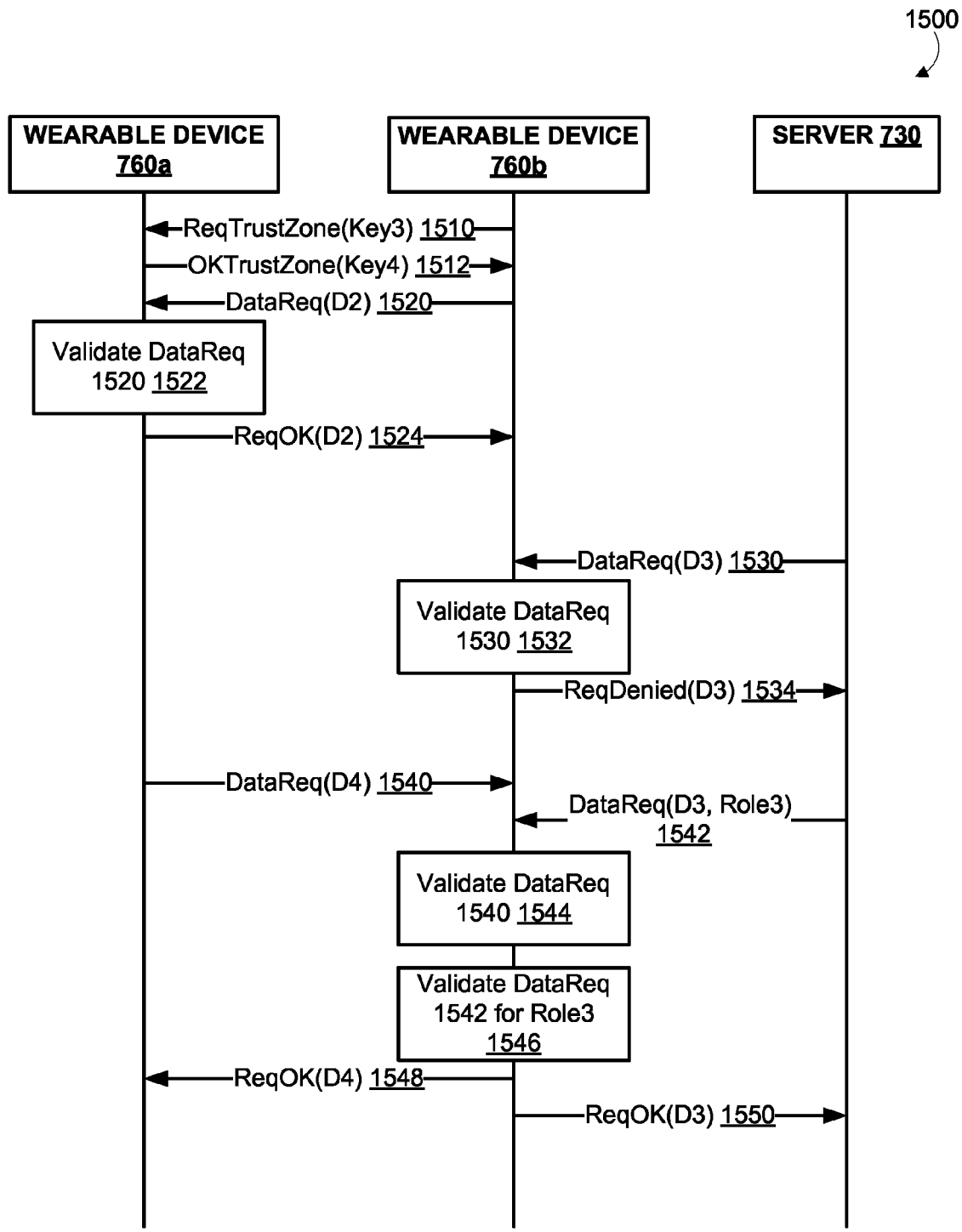
FIG. 15 depicts another example scenario with communication between wearable devices and a server.

At block 920, the wearable computing device can receive a request for a portion of the stored data, such as discussed herein with respect to FIGS. 13-15.

Figure 11:
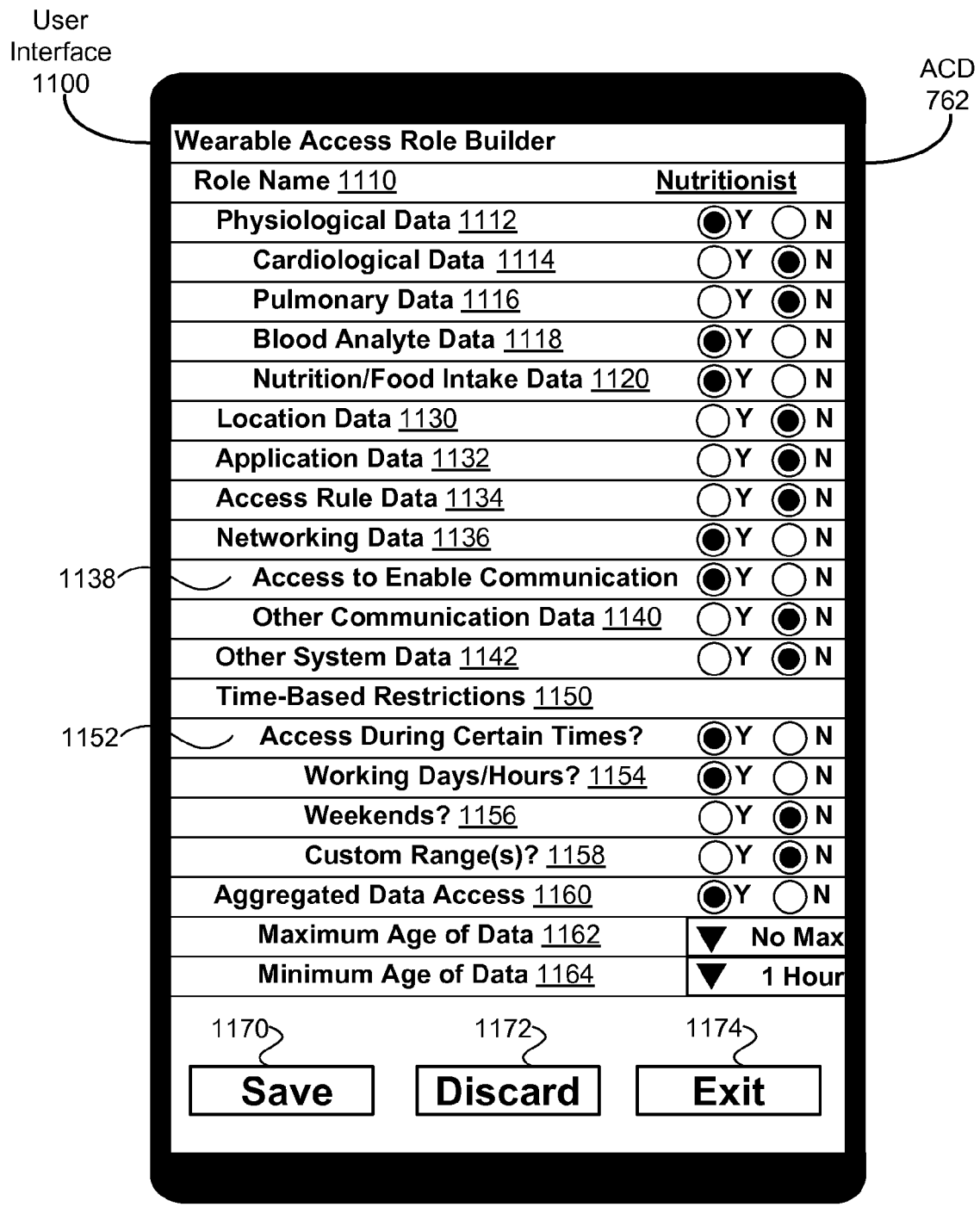
FIG. 11 depicts an example user interface for specifying roles.

At block 930, the wearable computing device can determine a designated role associated with the request for the portion of the stored data, such as discussed herein with respect to FIGS. 11, 14, and 15.

At block 940, the wearable computing device can determine one or more rules regarding access to the portion of the stored data based on the designated role, such as discussed herein in the context of at least FIGS. 11 and 13-15.

In some embodiments, the one or more rules regarding access to the portion of the stored data can include a plurality of rules specifying access to the stored data, where each rule of the plurality of rules is associated with a role of a plurality of roles, where the plurality of roles can include the designated role. Then, determining the one or more rules regarding access to the portion of the stored data based on the designated role can include determining one or more rules of the plurality of rules specifying access to the stored data that are associated with the designated role, such as discussed herein in the context of at least FIGS. 11 and 13-15. In particular embodiments, the plurality of roles further can include a wearer role and a manager role, where the wearer role provides access to at least some of the stored data, and where the manager role provides access to at least the one or more rules for each role of the plurality of roles, such as discussed herein in the context of at least FIG. 11. In more particular embodiments, the wearer role further can provide access to at least one rule of the one or more rules for each role of the plurality of roles, such as discussed herein in the context of at least FIG. 11.

In other embodiments, at least one rule of the one or more rules regarding access to the portion of the stored data can be related to providing aggregated data from the wearable computing device, such as discussed herein in the context of at least FIGS. 11 and 12. In particular embodiments, the at least one rule related to providing aggregated data can include a rule regarding providing the aggregated data without providing identifying data about the wearer, such as discussed herein in the context of least FIG. 12.

At block 950, the wearable computing device can determine a response to the request for the portion of the stored data using the wearable computing device by at least carrying out the procedures of blocks 952 and 954.

At block 952, the wearable computing device can determine whether the request is validated by at least applying the one or more rules to the request, such as discussed herein in the context of at least FIGS. 11-15. And, at block 954, the wearable computing device can, after determining that the request is validated, provide the requested portion of the stored data, discussed herein in the context of at least FIGS. 11-15.

In some embodiments, method 900 further can include specifying at least one rule of the one or more rules regarding access to the portion of the stored data using a user interface associated with the wearable computing device, such as discussed in the context of at least FIGS. 11 and 12.
Example Permission Schemes and Data Sharing for Wearable Devices FIG. 10 depicts example wearable device data 1010 and example wearable device roles 1030. Wearable device data 1010 can include physiological data 1012, aggregated data 1014, application data 1016, networking data 1018, access rule data 1020, and system data 1022. More, fewer, and/or different types of wearable device data 1010 are possible as well.

Physiological data 1012 can include data collected about a wearer, which can be a biological entity, wearing the wearable device. Example biological entities include, but are not limited to, humans. The wearable device can be configured with one or more sensors configured to obtain some or all of physiological data 1012 about the wearer. Example physiological data 1012 can include, but is not limited to, heart rate/pulse rate, blood pressure, blood chemistry (e.g., blood sugar levels, blood alcohol levels, blood oxygen levels), breathing rate, nutritional data such as specific dietary information or calorie counts, exercise information, and distances covered by the wearer while walking and/or running Other physiological data 1012 are possible as well.

Aggregated data 1014 can include data collected about a wearer over time; e.g., aggregated physiological data. For example, aggregated blood pressure data can include, but are not limited to, a collection of blood pressure readings, minimum/maximum/average blood pressure values over a period of time (e.g., a highest daily blood pressure value, an average of hourly blood pressure readings averaged over a day, week, or other interval), a count of blood pressure readings over or below a threshold value. Other examples of other types of aggregated physiological data are possible as well. Other data than physiological data can be aggregated as aggregated data 1014—for example, an amount of data received by (or sent from) a wearable device over a period of time, such as over one or more hours, days, weeks, months, and/or years, a count of requests for aggregated data over a period of time, a number of roles added, deleted, and/or utilized over a period of time.

Aggregated data 1014 can be provided without identifying information, such as a name of a wearer of the wearable device, a device identifier and/or networking identifier for the wearable device. As such, aggregated data 1014 provided without identifying information can be used, when so authorized, as part of a collection of information about wearable devices. The collection of information can be used to improve wearable device functionality, understand usage trends of the wearable device, determine health and/or other information over a population of wearable device users, and/or for other purposes. Other aggregated data 1014 are possible as well.

Application data 1016 can include data utilized by an application of a wearable device. Example application data 1016 include, but are not limited to, Internet data, such as data sent to and/or received from the Internet, data sent to and/or received from network(s) other than the Internet, documents, audio data, image data, video data, binary data, textual data, software, and diagrams. Other application data 1016 are possible as well.

Networking data 1018 can include data utilized by a wearable device to network with another device and/or communications network. Example networking data 1018 include, but are not limited to, network addresses, device addresses, other network protocol data (e.g., parameter data for utilizing a network protocol), and security data for utilizing a network (e.g., passwords, network keys). Most non-security networking data is intended to be shared to connect to other computers, so most networking data 1018 can be generally considered non-sensitive data when the wearable device is authorized to communicate with other devices. Other networking data 1018 are possible as well.

Access rule data 1020 can include rules that, when followed, allow or deny access to data. For example, an access rule can allow (or deny) access to: all data on the wearable device, all data of a particular data type (e.g., all physiological data), and/or specific data of a particular data type (e.g., blood sugar data of the physiological data).

For ease of administration, access rules can be packaged into roles—each role can have access to specific data of the wearable device. For example, a manager role can manage access to data by having access at least to access role data 1020, and so can set up rules and/or roles for other entities to access data on the wearable device.

As another example, a wearer role can have access at least to wearer-identifying information, such as a name, of the (usual) wearer of the wearable device. In some embodiments, a wearable device can have multiple wearers. For example, suppose a wearable device WD can be worn by a person P1 and other person(s), including P2. Then, the role of wearer P1 can allow access to wearer-identifying information for P1. Further, when P1 is wearing WD, then the role of wearer P1 can allow P1 to activate the wearer-identifying information for P1, and so indicate P1 as being a current wearer of WD. Then, if another wearer, e.g., person P2, later wears wearable device WD, P2 can activate wearer-identifying information for P2 to change the current wearer of WD from P1 to P2. Other access rules and/or roles of access rule data 1020 are possible as well, including but not limited to other access rules and/or roles discussed herein.

System data 1022 can include data utilized to execute the operating system and/or hardware of the wearable device. Examples of system data 1022 include but are not limited to storage allocation data, thread/process data, processor utilization information, hardware addresses and other information for hardware such as memory, sensors, devices, processors, etc., Other system data 1020 are possible as well Some or all of wearable device data 1010 can be classified as sensitive data using a number of different techniques. For example, wearable device data 1010 can be classified as sensitive data based generally on a type of data. One specification of sensitive data based on data type is indicated in FIG. 10; e.g., physiological data 1012 and access rules 1020 can be generally considered sensitive, system data 1022 can generally, but not always considered sensitive, application data 1016 can be considered sensitive or not sensitive based on the application (e.g., personal, financial, or security data used by an application can generally be considered sensitive, while data downloaded from a public network can generally be considered non-sensitive), and aggregated data 1014 and networking data 1018 each can be generally considered not sensitive. Other specifications of sensitive data based on data type are possible.

As another example, discussed in more detail below in the context of FIG. 12, different data items can be designated as sensitive, partially sensitive, or non-sensitive. Other techniques for designating data as sensitive data are possible as well; e.g., by specifying a sensitivity level, such as a range from 0 being non-sensitive to 100 being most sensitive.

FIG. 10 shows seven example wearable device roles 1030, including global role 1032, manager role 1034, wearer role 1036, medical professional role 1038, nutritionist rule 1040, device specialist role 1042, and application software (S/W) roles 1044. A role can be used to specify access to wearable device data, such as wearable device data 1010. More, fewer, and/or different wearable device roles 1030 are possible as well.

Each role can be associated with permissions and restrictions on wearable device data. The global role 1032 can be a role for an entity to have unlimited access to data on the wearable device; e.g., to permit the entity with global role 1032 to maintain, access, and perhaps provide any data on the wearable device. For example, global role 1032 can be held by an administrator of the wearable device in a similar fashion to an administrator having a "root" password of a UNIX® system.

Another example role is a manager role 1034, which has, among other permissions and restrictions, has unlimited access to rule data; e.g., access rule data 1020. With such access, an entity with manager role 1034 can control access by entities with other roles. That is, manager role 1034 can change access rule data 1020 for any particular role, and so control data access for the particular role. FIG. 11, discussed below in more detail, shows an example interface for allowing/restricting access to wearable device data on a per-role basis.

A wearer role 1036 can differ from global role 1032 and/or manager role 1034. For example, in situations where the wearer administers the wearable device, wearer role 1036 can be permitted to have unlimited access to data on the global device; that is, global role 1032 and wearer role 1036 can have the same set of permissions that allow unlimited access to data. In another example, the wearer may not have unlimited access to data on the global device, but can have unlimited access to access rule data 1020 to add, delete, change, and review roles; that is, wearer role 1036 can have the same unlimited access to access rule data 1020 as provided to manager role 1034. In the example shown in FIG. 10, wearer role 1036 has read-only access to access rule data 1020 which allows wearer role 1036 to review, but not change (e.g., add, delete, or update) access rule data 1020. The read-only access may apply to only one role; e.g., access to access rule data 1020 for wearer role 1036, applicable to some but not all roles, or may be applicable to enable access to all of access rule data 1020.

Restrictions/permissions for wearer role 1036 to access other types of data, such as physiological data 1012, aggregated data 1014, application data 1016, and networking data 1018, can be controlled by global role 1032 and/or manager role 1034 via controlling access rule data 1020 for wearer role 1036.

Other example roles—medical professional role 1038, nutritionist role 1040, device specialist role 1042, and application software role 1044—are shown in FIG. 10. Each role has access to some data of the wearable device and is denied access to other data of the wearable device. In some cases, a role; e.g., a "locked out" role, can be established with no access to any data for the wearable device—the locked out role can be assigned to untrustworthy entities, or other entities that should not be permitted any access to data of the wearable device. Many other roles and corresponding rules are possible as well.

FIG. 11 depicts user interface 1100 for specifying roles. User interface 1100 is shown being utilized on associated computing device (ACD) 762. In other embodiments, some or all of the herein-described functionality of user interface 1100, can be provided on a wearable device, a server, and/or on one or more other computing devices.

User interface 1100 can provide an interface for adding, reviewing, updating, and/or deleting roles, including adding, reviewing, updating, and/or deleting access rule data; e.g., access rule data 1030, for one or more roles. As shown in FIG. 11, a "nutritionist" role is shown with some access to physiological data, no access to location data, application data, or access rule data, some access to networking data, and is able to set time-based restrictions related to aggregating data. In some embodiments, user interface 1100 can only be utilized by an entity with an appropriate role; e.g., a role permitting access to access rule data 1020.

User interface 1100 includes an interface for specifying a role name 1100 and access settings for the named role. The access settings include physiological data access setting 1112, location data setting 1130, application data setting 1132, access rule data setting 1134, networking data setting 1136, other system data setting 1142, time-based restrictions 1150, and aggregated data access setting 1160. As shown in FIG. 11, user interface 1100 also includes three control buttons: save button 1170 to save any changes made to the role, discard button 1172 to not save, or discard, any changes made to the role, and exit button 1174 to exit user interface 1100.

In the example user interface 1100, selecting a "Y" for Yes allows access to a particular type of data and selecting an "N" for No denies access to the particular type of data. Other selections and techniques for selecting access to types of data are possible as well. Using the Y/N selections, access can be denied, partially granted, or completely granted to a type of data. For example, to deny access to physiological data 1012, physiological data setting 1112 can be set to "N" for no access. In the example shown in FIG. 11, physiological data 1012 has four sub-types of data: cardiological data, pulmonary data, blood analyte data, and nutrition/food intake data. Partial access to physiological data 1012 can be granted by selecting "Y" for physiological data setting 1112 to allow access to physiological data 1012 and subsequently selecting at least one "Y" setting and at least one "N" setting for physiological data sub-type settings 1114, 1116, 1118, and 1120. Then, in the example shown in FIG. 11, complete access to physiological data 1012 can be granted by selecting "Y" for each of settings 1112, 1114, 1116, 1118, and 1120; i.e., granting access to physiological data generally and each of the physiological data sub-type settings.

In the example shown in FIG. 11, a role whose name is "Nutritionist" is shown given partial access to physiological data 1012 using user interface 1100. This partial access is granted by selecting the "Y" for Yes radio button of physiological data access setting 1112. Then, after selecting "Y" for physiological data access setting 1112, settings for different types of physiological data are presented as part of user interface 1100. FIG. 11 shows example settings for different types of physiological data including cardiological data setting 1114, pulmonary data setting 1116, blood analyte data setting 1118, and nutrition/food intake data setting 1120. Partial access to physiological data 1012 is granted for the "Nutritionist" role by allowing access to blood analyte data and nutrition/food intake data by selecting "Y" for respective blood analyte data setting 1118 and nutrition/food intake data setting 1120. However, access to cardiological data and pulmonary data is denied for the "Nutritionist" role by selecting "N" for respective cardiological data setting 1114 and pulmonary data setting 1116.

The "Nutritionist" role is denied access to location data, application data, access rule data, and other system data as indicated by the respective "N" selections of location data setting 1130, application data setting 1132, access rule data setting 1134, and other system data setting 1142.

The "Nutritionist" role is granted partial access to networking data setting 1136 as indicated by the "Y" selections of respective networking data setting 1136 and access to enable communication setting 1138 and a "N" selection to other communication data setting 1140, to deny access to communication data that is not necessary to enable communications. Other sub-types of networking data are possible as well.

Access to data can be provided based on one or more times of day, days of the week, and/or other time-based specifications. Time-based restrictions 1150 include time-based restriction setting 1152, working days/hours setting 1154, weekends setting 1156, and custom range setting 1158. Time-based restriction setting 1152 can be set to Y/Yes to enable time-based restrictions on wearable device data, and set to N/No to disable time-based restrictions on wearable device data. FIG. 11 shows three specific time-based setting on wearable device data: working days/hours setting 1154 for allowing or denying access to wearable device data during working days and hours, weekends setting 1156 for allowing or denying access to wearable device data during weekends, and custom range setting 1158 for allowing or denying access to wearable device data during one or more custom ranges of time; e.g., allow/deny access during a scheduled appointment, during certain times of the day, during certain days of the week, for a range of days, weeks, months, and/or years. In some embodiments, user interface 1100 can be configured to specify ranges of times corresponding to working hours, working days, and weekends.

In the example shown in FIG. 11, time-based restriction setting 1152 is set to Y to restrict the Nutritionist role to accessing wearable device data based on time. Then, as working days/hours setting 1154 is set to Y, the Nutritionist role is allowed access to wearable device data during working hours and working days. As each of weekends setting 1156 and custom range setting 1158 are set to N, the Nutritionist role is denied access outside of working hours and working days.

Aggregated data access setting 1160 can be used to allow or deny access to aggregated data. In some embodiments, sub-types of aggregated data can be specified; for example, aggregated physiological data, aggregated location data, aggregated networking data. In other embodiments, user interface 1100 can be utilized to specify rules for data aggregation, such as rules to aggregate only blood analyte data, aggregate all physiological data and networking data, but do not aggregate any location data, aggregate selected sub-types of physiological data and selected sub-types networking data collected during certain time ranges, etc.

Data can be aggregated based on a minimum and a maximum age; e.g., data between the minimum age and the maximum age is aggregated, while data under the minimum age or over the maximum age is separated from aggregated data. For example, if location data is aggregated for a minimum age of 1 day and a maximum age of 1 month, then aggregated data would store information about location(s) of the wearable device from 1 day ago until 1 month ago. Data under the minimum age can be stored separately from aggregated data, and may or may not be accessible; for example, immediate location data may not be accessible unless specifically authorized or during a wearer-indicated emergency. Data older than the maximum age can be discarded as being out of date and/or having already been saved elsewhere as needed.

In the example shown in FIG. 11, a minimum age to aggregate data is 1 hour and a maximum age is not specified (No Max). In the case of no maximum age being specified, aggregated data can be stored until there is no more storage available on the wearable device for storing aggregated data. To free storage when no more aggregated data storage is available, aggregated data can be deleted based on an age of the aggregated data, a type of the aggregated data, a size of aggregated data items, and/or deleted based on other criteria. Many other types and controls for aggregated data are possible as well.

Data specifying access to wearable device data, such as data for wearable device roles 1030 or data specified using user interface 1100 regarding sensitivity of data discussed in the context of FIG. 12, can be stored in a number of locations. As indicated in FIG. 11, data specifying access to wearable device data can be stored on one or more associated computing devices like associated computing device 762. In some embodiments, data specifying access to wearable device data can be stored on the wearable device and perhaps other wearable devices. In other embodiments, data specifying access to wearable device data can be stored on one or more other devices, such as server 730 or other computing devices. In still other embodiments, data specifying access to wearable device data can be stored on multiple devices; e.g., on the wearable device and on associated computing device 762.

Data specifying access to wearable device data can be provided using one device and then transmitted to another device for storage and/or usage. For example, user interface 1100 of associated computing device 762 can be used to input data to specify access for one or more roles and/or otherwise specify access to wearable device data. The input data can then be sent to another device; e.g., the wearable device, which can then store and/or use the data to specify access. In other embodiments, associated computing device 762 can be used to input and store data to specify access, and then transmit the data to the wearable device. In still other embodiments, all communication to the wearable device can pass through another computing device; e.g., associated computing device 762. Then, the other computing device can store and use the rules and/or role data to allow or deny access to wearable device data. Other embodiments regarding storage and/or usage of data for controlling access to wearable device data are possible as well.

As another example, user interface 1100 or another user interface operating on another device, such as server 730, can be used to input data to specify access for one or more roles and/or otherwise specify access to wearable device data without direct knowledge by a wearer. For example, technicians at server 730 can be requested to build roles for one or more users at server 730 and then download the generated rules to devices; e.g., one or more wearable devices 700, 760a-760c. These rules can be used to provide requested functionality. For example, a hospital may want to define access rules for various hospital roles, such as "physician", "registered nurse", "hospital administrator", etc. Then, user interface 1100 operating on server 730 can be used to generate the rules for the hospital roles and then download the generated rules to wearable devices used by hospital personnel to provide uniform access rules throughout the hospital. As another example, rules can be developed to address security concerns or to fix data and/or software errors; for example, access to physiological data may be temporarily denied while server(s) storing the physiological data are undergoing maintenance, being upgraded, undergoing a security audit and/or for other reasons. Then, to temporarily deny such access, user interface 1100 operating on server 730 can be used to generate changes to rules to deny access to physiological data; e.g., for a custom period of time to fix a bug or address a one-time concern, for given periods corresponding to maintenance windows. Many other examples of rules being generated and/or updated by persons other than a wearer are possible as well.

The input data can then be sent to another device; e.g., the wearable device, which can then store and/or use the data to specify access. In other embodiments, associated computing device 762 can be used to input and store data to specify access, and then transmit the data to the wearable device. In still other embodiments, all communication to the wearable device can pass through another computing device; e.g., associated computing device 762. Then, the other computing device can store and use the rules and/or role data to allow or deny access to wearable device data. Other embodiments regarding storage and/or usage of data for controlling access to wearable device data are possible as well.

FIG. 12 depicts user interface 1200 for defining sensitive data. User interface 1200 is shown being utilized on associated computing device 762. In other embodiments, some or all of the herein-described functionality of user interface 1200, can be provided on a wearable device, a server, and/or on one or more other computing devices. User interface 1200 includes an interface for specifying settings of different types of data as sensitive, non-sensitive, or partially sensitive. In some embodiments, user interface 1200 can only be utilized by an entity having an appropriate role; e.g., a role permitting access to access rule data 1020 (as controlling sensitivity of data and/or configuring aggregation of data is one technique to control access to data on the wearable device), separate role(s) for that allows access to controlling the sensitivity of data and/or for configuring data aggregation.

The sensitivity settings include physiological data sensitivity setting 1212, location data sensitivity setting 1214, application data sensitivity setting 1216, access rule data sensitivity setting 1230, networking data sensitivity setting 1232, and system data sensitivity setting 1234.

In the example interface 1210 for specifying data as sensitive data, selecting a "Y" for Yes indicates the type of data is sensitive, selecting a "N" for No indicates the type of data is not sensitive, and selecting a "Some" indicates that the data is partially-sensitive. Physiological data sensitivity setting 1212 allows specification of the sensitivity of physiological data 1012, shown in the example of FIG. 12 with a "Y" to indicate that all of physiological data 1012 is considered to be sensitive data. Location data sensitivity setting 1214 allows specification of the sensitivity of a location of the wearable device, set in the example shown in FIG. 12 to "Y" to indicate that all location data is considered to be sensitive data. In some scenarios, a sensitivity setting can be overridden—for example, sensitive location data can be provided in an emergency situation, such as indicated during an emergency call to 911.

When "Some" is selected, additional selections for designating sensitivity for sub-types of the selected type of data can be provided by interface 1210. For example, in FIG. 12, application data sensitivity setting 1216 controlling sensitivity of application data 1016 is set to "Some", and an interface for selections for internet data sub-type sensitivity setting 1218 and local data/documents sub-type sensitivity setting 1220 is displayed.

Networking data sensitivity setting 1232, controlling sensitivity to networking data 1018, is indicated in the example shown in FIG. 12 to be set to "N" indicating all networking data 1018 is considered as non-sensitive data. Access rule data sensitivity setting 1230 and system data sensitivity setting 1234, controlling respective sensitivities of access rule data 1020 and of system data 1022, are both indicated in the example shown in FIG. 12 to be set to "Y" indicating all access rule data 1020 and all system data 1022 are considered as sensitive data. Other example selections and techniques for designating sensitivity are possible as well.

FIG. 12 also shows an interface 1240 for configuring data aggregation. Data aggregation can include collating/storing raw data, periodic collection/sampling of data, storing statistics about a data population (e.g., average, maximum and minimum blood pressures over one or more hours, days, weeks, etc.; calories-consumed trends over several months), and other storage techniques. Aggregated data can be sent to another device periodically, upon request by the wearer of the wearable device, upon receiving an authorized request from the other device, when certain conditions are present on the wearable device (e.g., a buffer storing aggregated data is over a threshold percentage of occupancy such as at/over 90%/95% occupied), or under other conditions.

Data aggregation settings 1240 used for configuring data aggregation include aggregation-enabled setting 1242, initiate sending setting 1244, aggregated data destination 1246, provide identifying data setting 1248, aggregation of physiological data setting 1250, maximum aggregation data buffer size 1252, minimum aggregation waiting period setting 1254, and a maximum aggregation period setting 1256.

Aggregation-enabled setting 1242 can control whether or not the wearable device aggregates data. In the example shown in FIG. 12, aggregation-enabled setting 1242 is set to "Y" to indicate that data aggregation is enabled for the wearable device. If aggregation-enabled setting 1242 was set to "N", data aggregation would be disabled for the wearable device.

Initiate sending setting 1244 can control whether or not the wearable device pushes aggregated data; that is, the wearable device sends aggregated data to another device without a specific request. In the example shown in FIG. 12, initiate sending setting 1244 is set to "Y" to indicate that the wearable device can push aggregated data. If initiate sending setting 1244 were set to "N", then the wearable device would not initiate sending of aggregated data, and would instead send aggregated data only upon request, that is, when "pulled" to send the aggregated data to another device by the request. In particular embodiments, if initiate sending setting 1244 is set to "Y", the wearable device can be configured as "push-only"—that is, configured to ignore requests to pull aggregated data from other devices.

Aggregated data destination 1246 can specify a network location for sending aggregated data, shown in FIG. 12 as the example partially qualified domain name "AggDataMachine". In other embodiments, a fully qualified domain name, an Internet Protocol (IP) address, a media access control (MAC) address, a URL, and/or other type of network address can be used to specify aggregated data destination 1246. In some embodiments, when initiate sending setting 1244 is set to "Y", then the wearable device can push aggregated data to computing device(s) at the specified network location of aggregated data destination 1246. In other embodiments, when initiate sending setting 1244 is set to "N", then the wearable device can pull aggregated data only upon request from computing device(s) at the specified network location aggregated data destination 1246.

In still other embodiments, aggregated data destination 1246 can allow specification of multiple destinations; perhaps including a primary aggregated data destination and one or more secondary aggregated data destinations. Other examples for aggregated data destination 1246 are possible as well.

Provide identifying data setting 1248 can indicate whether or not identifying data, such as, but not limited to wearer name, wearer address, and wearable device name data, are provided with aggregated data. In the example shown in FIG. 12, provide identifying data setting 1248 is set to "N" to indicate that identifying information is not provided with aggregated data. If provide identifying data setting 1248 was set to "Y", identifying information would be provided with aggregated data.

Aggregation of physiological data setting 1250 can indicate whether or not physiological data is aggregated. In the example shown in FIG. 12, aggregation of physiological data setting 1250 is set to "Y" to indicate that physiological data 1012 can be aggregated by the wearable device. If aggregation of physiological data setting 1250 was set to "N", physiological data 1012 would not be aggregated by the wearable device. If aggregation of physiological data setting 1250 was set to "Some", some but not all of physiological data 1012 could be aggregated by the wearable device; i.e., physiological data 1012 can be aggregated specified on a per-sub-type of physiological data basis, such as cardiological data, pulmonary data, blood analyte data, and nutrition/food intake data as shown in FIG. 12. In other examples, settings for aggregation of other types of data; e.g., location data, can be specified as well.

Maximum aggregation data buffer size 1252 can specify a maximum amount of storage allocated on the wearable device is allocated for aggregated data. In the example shown in FIG. 12, maximum aggregation data buffer size 1252 is set to "1 MB" to indicate that one megabyte of storage of the wearable device is allocated to store aggregated data. Other sizes for aggregated data buffers are possible as well.

In some embodiments, a minimum aggregation data buffer size can be specified to indicate a minimum amount of storage of the wearable device allocated to aggregating data. In other embodiments, one or more thresholds T1, T2 . . . related to initiating sending of aggregated data based on the amount of data stored in aggregation data buffer can be specified; e.g., sending of aggregated data can be initiated if aggregation data buffer stores T1 or more bytes of aggregated data, if aggregation data buffer is T2% or more occupied with aggregated data.

Minimum aggregation waiting period setting 1254 can specify a minimum amount of time after data is collected before the data is available as aggregated data. For example, if minimum aggregation waiting period setting 1254 is set to WP (e.g., 1 hour) and data is collected at time T, the collected data will not be available for aggregation until time T+WP (or later).

If minimum aggregation waiting period setting 1254 is set to some waiting period WP units of time, then the wearable device can buffer data for aggregation for at least WP units of time in a temporary buffer or other storage separate from storage used for the aggregated data. Then, after at least WP units of time, data can be copied from the temporary buffer to the storage used for the aggregated data. In this example, minimum aggregation waiting period setting 1254 can be used to prevent against real-time tracking/observation of a wearer via aggregated data, as all aggregated data will be at least WP units of time old.

In the example shown in FIG. 12, minimum aggregation waiting period setting 1254 is set to "1 Hour". When minimum aggregation waiting period setting 1254 is set to "0", then data collected at time T can be made immediately available as aggregated data.

Maximum aggregation period setting 1256 can specify a maximum amount of time, or age, of data to be aggregated. In the example shown in FIG. 12, maximum aggregation waiting period setting 1256 is set to "10 Days"; that is, any aggregated data 10 days old or older can be deleted. When maximum aggregation waiting period setting 12656 is set to "No Maximum" (or an equivalent value), then aggregated data may be kept indefinitely or deleted for reasons other than an age of aggregated data, such as being deleted after being sent from the wearable device or because aggregated data storage is full.

As shown in FIG. 12, user interface 1200 also includes three control buttons similar to those shown in FIG. 11: save button 1270 to save any changes made to the sensitivity settings and/or data aggregation configuration, discard button 1272 to not save, or discard, any changes made to the sensitivity settings and/or data aggregation configuration, and exit button 1274 to exit user interface 1200. FIG. 12 also shows restore defaults button 1276 for restoring sensitivity settings and data aggregation settings to default values; e.g., values of sensitivity settings and data aggregation settings as originally set by the manufacturer or provider of a wearable device and/or an associated computing device.

As discussed above in the context of data specifying access to wearable device data and FIG. 11, data designating sensitivity and/or data configuring data aggregation can be stored in a number of locations; e.g., on one or more wearable devices, associated computing devices, servers, and/or other computing devices. Other data for designating sensitivity and/or configuring aggregation of data are possible as well.

FIG. 13 is a flow chart for method 1300 for providing data based on roles. Method 1300 can begin at block 1310, where a request can be received for data D of at least type T associated with wearable device WD. For example, the request can be received from a device D1.

At block 1320, a role R can be associated with the request of block 1310.

At block 1330, if role R granted access to data of type T, then method 1300 can proceed to block 1340; otherwise, as role R did not grant access to data of type T, then method 1300 can proceed to block 1344.

At block 1340, if time of day or time of data restrictions restrict access to data D, then method 1300 can proceed to block 1344; otherwise, as time of day or time of data restrictions did not restrict access to data D, then method 1300 can proceed to block 1342.

At block 1342, data D can be provided in response to the request of block 1310; e.g., a message including data D can be sent to the device D1. After providing data D, method 1300 can proceed to block 1350.

At block 1344, the request of block 1310 can be denied. Data D is not provided in this case. In some embodiments, a message can be sent; e.g., to device D1, to indicate that the request of block 1310 has been denied; while in other embodiments, the denial can be silent and no message in sent in response to a denied request. After denying the request, method 1300 can then proceed to block 1350.

At block 1350, a determination can be made whether more requests for data associated with wearable device WD are available. If more requests for data associated with wearable device WD are available, then method 1300 can proceed to block 1310; otherwise, method 1300 can end.

In some embodiments, all of the procedures of method 1300 can be carried out by wearable device WD. In other embodiments, the procedures of method 1300 can be carried out at least in part by other devices than wearable device WD. For example, if role data for wearable device WD is stored on an associated computing device ACD1, then WD and ACD1 can cooperate to carry out method 1300. In still other embodiments, the procedures of method 1300 can be carried out by device(s) other than wearable device WD; e.g., if the data requested at block 1310 and data used to carry out method 1300 (e.g., access rules and/or role data) are all stored on ACD1, then ACD1 can be configured to carry out method 1300.

FIG. 14 depicts scenario 1400 with communication between wearable device 760*a* and server 730. Wearable device 760*a* and server 730 can be connected as indicated in FIG. 7B. Intermediate devices, such as associated computing device 762 and devices in network 720 are not shown in the communication flows depicted in FIG. 14.

Scenario 1400 begins with server 730 sending request trust zone message 1410 with a key Key1 to request a trust zone be established between wearable device 760*a* and server 730. A trust zone is established to permit device-to-device communication without per-application keys or other security; that is, all messages between devices within a trust zone are assumed to be secure after the trust zone is established. These messages can be encrypted or otherwise secured to prevent outside devices from eavesdropping on messages within the trust zone; for example, messages within a trust zone destined to wearable device 760*b* can be encrypted or otherwise secured using Key1. For example, Key1 can be a public key associated with server 730. Wearable device 760*a* can use Key1 to authenticate that messages, signatures, and/or other communications are truly sent from server 730. However, in scenario 1400, server 730, access to data on wearable device 760*a* based on roles, even if a trust zone is established.

Scenario 1400 continues with wearable device 760*a* sending OK Trust Zone message 1412 with key Key2 that server 730 can use to authenticate that messages, signatures, and/or other communications are truly sent from wearable device 760*a*. After server 730 receives OK Trust Zone message 1412, a trust zone is established between wearable device 760*a* and server 730.

In scenario 1400, associated computing device 762 is not assumed to be part of the trust zone between wearable device 760*a* and server 730. In other scenarios, intermediate device(s), such as associated computing device 762, can be part of a trust zone as well.

Scenario 1400 continues with server 730 communicating send software (S/W) message 1420 with patch Patch1 to wearable device 760*a*. Patch1 can be considered to be system data and/or application data. No role information is provided as part of send software message 1420, as server 730 is providing data to wearable device 760*a* (as opposed to accessing data from wearable device 760*a*). Upon reception of Patch1, wearable device 760*a* can scan Patch1 as needed for viruses, prior application, etc. At block 1422, wearable device 760*a* can apply Patch1 to software of the wearable device. FIG. 14 indicates that after applying Patch1, wearable device 760*a* can send software updated message 1424 to inform server 730 that Patch1 has been applied.

Scenario 1400 continues with wearable device filling an aggregated data buffer at block 1430. In scenario 1400, wearable device 760*a* is configured to push aggregated data to server 760 when the aggregated data buffer is full. Therefore, wearable device 760*a* generates send data message 1432 with aggregated data AggData from the full aggregated data buffer, along with an ACK indication requesting acknowledgement of the send data message. Wearable device 760*a* then sends send data message 1432 to server 730. In other scenarios, multiple send data messages can be used to send aggregated data from the full aggregated data buffer to server 730. Upon reception of send data message 1432, server 730 can obtain aggregated data AggData and sends data acknowledgment (DataAck) message 1434 as requested by wearable device 760*a*.

Server 730 then determines a use for data D1 on wearable device 760*a*. To obtain data D1, server 730 generates data request message 1440 requesting data D1 for an entity having role Role1. Server 730 then sends data request message 1440 to wearable device 760*a*. At block 1442, wearable device 760*a* attempts to validate data request message 1440 for role Role1, but determines that Role1 does not have permissions to access data D1, and so data request message 1440 is invalid. For example, wearable device 760*a* can access rules related to accessing data based on role Role1, such as roles designated using user interface 1100 and discussed above in the context of at least FIG. 11. Then, based on the accessed rules related to role Role1, wearable device 760*a* can determine if Role1 has access to data D1; for example, based on rules specifying access for role Role1 to various types and/or sub-types of data stored on wearable device 760*a*. In scenario 1400, wearable device 760*a* can determine that Role1 does not have access to data D1 based on the rules specifying access for role Role1, and so determine the request of associated with data request message 1440 is invalid.

After determining that data request message 1440 is invalid, wearable device 760*a* generates and send request denied message 1444 to server 730 to indicate requesting data D1 for role Role1 is invalid and so has been denied.

Server 730 then determines to re-request data D1 with another role, Role2. Server 730 generates data request message 1450 requesting data D1 for an entity having role Role2. Server 730 then sends data request message 1450 to wearable device 760*a*. At block 1452, wearable device 760*a* attempts to validate data request message 1450 for role Role2, and determines that Role2 does have permissions to access D1, and so data request message 1450 is valid.

For example, wearable device 760*a* can access rules related to accessing data based on role Role2, such as roles designated using user interface 1100 and discussed above in the context of at least FIG. 11. Then, based on the accessed rules related to role Role2, wearable device 760*a* can determine if Role2 has access to data D1; for example, based on rules specifying access for role Role1 to various types and/or sub-types of data stored on wearable device 760a. In scenario 1400, wearable device 760a can determine that Role2 does have access to data D1 based on the rules specifying access for role Role2, and so determine the request of associated with data request message 1450 is valid.

After determining that data request message 1450 is valid, wearable device 760a obtains data D1, generates request OK message 1454 with data D1, and sends request OK message 1454 to server 730. Upon reception, server 730 obtains data D1 from request OK message 1454.

Later in scenario 1400, at block 1460, wearable device 760a generates a status report StatusReport. For example, wearable device 760a can generate status reports periodically, after sending aggregated data to another device; e.g., as sent in send data message 1432, or for some other reason. Wearable device 760a can send StatusReport to server 730 via send data message 1462 with a NOACK indication, indicating that no acknowledgment from server 730 is request. Upon reception, server 730 can obtain StatusReport from send data message 1462. Scenario 1400 can then end.

FIG. 15 depicts scenario 1500 with communication between wearable devices 760a, 760b and server 730. Wearable devices 760a, 760b and server 730 can be connected as indicated in FIG. 7B. Intermediate devices, such as associated computing device 762 and devices in network 720 are not shown in the communication flows depicted in FIG. 15.

Scenario 1500 begins with wearable device 760b sending request trust zone message 1510 with a key Key3 to request a trust zone be established between wearable devices 760a and 760b. Trust zones are discussed above in more detail; for example, see the discussion of FIG. 14.

Key3 can, for example, be a public key associated with wearable device 760b. Wearable device 760a can use Ke31 to authenticate that messages, signatures, and/or other communications are truly sent from wearable device 760b.

Scenario 1500 continues with wearable device 760a sending OK Trust Zone message 1512 with key Key3 to wearable device 760b, so that wearable device 760b can authenticate that messages, signatures, and/or other communications are truly sent from wearable device 760a. After wearable device 760b receives OK Trust Zone message 1512, a trust zone is established between wearable device 760a and server 730. In scenario 1500, after the trust zone is established between wearable devices 760a and 760b, data can be accessed by either wearable device in the trust zone without consideration of a role of a requesting entity.

In scenario 1500, associated computing device 762 is not assumed to be part of the trust zone between wearable devices 760a and 760b. In other scenarios, intermediate device(s), such as associated computing device 762, can be part of a trust zone as well. Further, server 730 is not part of the trust zone established between wearable devices 760a and 760b. Additionally, all requests for data in scenario 1500 involve a request for sensitive data; that is, each of data requests 1520, 1530, 1540, and 1542 shown in FIG. 15 request some type of sensitive data.

Scenario 1500 continues with wearable device 760b requesting data D2 from wearable device 760a using data request message 1520. Upon reception, wearable device 760a attempts to validate data request 1520 at block 1522. Data request 1520 can be validated by wearable device 760a without role data since: (a) data request 1520 came from wearable device 760b, and (b) wearable devices 760a and 760b have established a trust zone. After validating data request 1520, wearable device 760a can obtain data D2, generate request OK message 1524 with data D2, and send request OK message 1524 to wearable device 1530.

Scenario 1500 continues with server 730 then determines a use for data D3 on wearable device 760b. To attempt to obtain data D3, server 730 generates data request message 1530 requesting data D3 without role data. Server 730 then sends data request message 1530 to wearable device 760b. At block 1532, wearable device 760b attempts to validate data request message 1530, but determines that server 730 cannot access data D3 without the appropriate role data, and so data request message 1530 is invalid. After determining that data request message 1530 is invalid, wearable device 760b generates and sends request denied message 1534 to server 730 to indicate that the request for data D3 has been denied as invalid.

Requests from within a trust zone and outside a trust zone can be processed at or about the same time. For example, scenario 1500 continues with server 730 determining to re-request data D3 from wearable device 760b for an entity having role Role3. At approximately the same time, wearable device 760a determines to request data D4 from wearable device 760b. Then, at or about the same time, wearable device 760a generates and sends data request 1540 for data D4 to wearable device 760b and server 730 generates and sends data request 1542 to request data D3 for the entity having role Role3 to wearable device 760b.

Upon reception of messages 1540 and 1542, wearable device 760b attempts to validate each message. At block 1542, data request 1540 for data D4 can be validated by wearable device 760b without role data since: (a) data request 1540 came from wearable device 760a, and (b) wearable devices 760a and 760b have established a trust zone. At block 1546, data request 1542 for data D3 can be validated by wearable device 760b since: (a) data request 1542 included role data Role 3, and (b) role Role3 has access to the data in D3. Role Role3 can be determined to have access to the data in D3 using the techniques discussed above at least in the context of validating data requests 1440 and 1450 of FIG. 14.

After validating data request 1540, wearable device 760b obtains data D4, generates request OK message 1548 with data D4, and sends request OK message 1548 to wearable device 760a. Further, after validating data request 1542, wearable device 760b obtains data D3, generates request OK message 1550 with data D3, and sends request OK message 1550 to server 730. Scenario 1500 can then end.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's physiology, medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as non-transitory computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for provided for explanatory purposes and are not intended to be limiting, with the true scope being indicated by the following claims.

What is claimed is:

1. A method, comprising:
   obtaining, using one or more sensors on a wearable computing device, physiological parameters of a wearer of the wearable computing device, wherein the obtained physiological parameters comprise at least one of a pulse rate, breathing rate, blood pressure, skin temperature, or analyte concentration;
   storing data on the wearable computing device, wherein the stored data comprises the obtained physiological parameters of the wearer of the wearable computing device;
   after storing the data on the wearable computing device, receiving, at the wearable computing device, a request for a portion of the previously stored data;
   determining a designated role associated with the request for the portion of the previously stored data;
   determining, using the wearable computing device, one or more rules regarding access to the portion of the previously stored data based on the designated role; and
   determining, using the wearable computing device, a response to the request for the portion of the previously stored data by at least:
     determining whether the request is validated by at least applying the one or more rules to the request, and
     after determining that the request is validated, providing the requested portion of the previously stored data.

2. The method of claim 1, wherein the stored data comprises sensitive data, and wherein the sensitive data comprises the obtained physiological parameters of the wearer of the wearable computing device.

3. The method of claim 2, wherein the sensitive data is defined based on one or more designations regarding sensitive data.

4. The method of claim 3, wherein at least one designation of the one or more designations regarding sensitive data relates to a time for accessing sensitive data.

5. The method of claim 3, wherein at least one designation of the one or more designations regarding sensitive data relates to a time when sensitive data was generated.

6. The method of claim 1, wherein the one or more rules regarding access to the portion of the stored data comprise a plurality of rules specifying access to the stored data based on a plurality of roles, wherein each rule of the plurality of rules is associated with a role of the plurality of roles, wherein the plurality of roles comprise the designated role, and wherein determining the one or more rules regarding access to the portion of the stored data based on the designated role comprises determining one or more rules of the plurality of rules specifying access to the stored data that are associated with the designated role.

7. The method of claim 6, wherein the plurality of roles further comprise a wearer role and a manager role, wherein the wearer role provides access to at least some of the stored data, and wherein the manager role provides access to at least the one or more rules associated with each role of the plurality of roles.

8. The method of claim 7, wherein the wearer role further provides access to at least one rule of the one or more rules associated with each role of the plurality of roles.

9. The method of claim 1, wherein at least one rule of the one or more rules regarding access to the portion of the stored data is related to providing aggregated data by the wearable computing device.

10. The method of claim 9, wherein the at least one rule related to providing aggregated data comprises a rule regarding providing the aggregated data without providing identifying data about the wearer.

11. The method of claim 1, further comprising:
specifying at least one rule of the one or more rules regarding access to the portion of the stored data using a user interface associated with the wearable computing device.

12. The method of claim 1, wherein the stored data further comprises data about a context of the wearer and/or data about an environment for the wearer.

13. A wearable computing device, comprising:
one or more sensors;
a processor; and
a non-transitory computer readable medium configured to store at least data and executable instructions, wherein the executable instructions, when executed by the processor, cause the wearable computing device to perform functions comprising:
obtaining, using the one or more sensors, physiological parameters of a wearer of the wearable computer device, wherein the obtained physiological parameters comprise at least one of a pulse rate, breathing rate, blood pressure, skin temperature, or analyte concentration,
storing data in the non-transitory computer readable medium, wherein the stored data comprises the obtained physiological parameters of the wearer of the wearable computing device,
after storing the data in the non-transitory computer readable medium, receiving a request for a portion of the previously stored data,
determining a designated role associated with the request for the portion of the previously stored data,
determining one or more rules regarding access to the portion of the previously stored data based on the designated role, and
determining a response to the request for the portion of the previously stored data by at least:
determining whether the request is validated by at least applying the one or more rules to the request, and
after determining that the request is validated, providing the requested portion of the previously stored data from the non-transitory computer readable medium.

14. The wearable computing device of claim 13, wherein the stored data comprises sensitive data, and wherein the sensitive data comprises the obtained physiological parameters of the wearer of the wearable computing device.

15. The wearable computing device of claim 13, wherein the one or more rules regarding access to the portion of the stored data comprise a plurality of rules specifying access to the stored data based on a plurality of roles, wherein each rule of the plurality of rules is associated with a role of the plurality of roles, wherein the plurality of roles comprise the designated role, and wherein determining the one or more rules regarding access to the portion of the stored data based on the designated role comprises determining one or more rules of the plurality of rules specifying access to the stored data that are associated with the designated role.

16. The wearable computing device of claim 15, wherein the plurality of roles further comprise a wearer role and a manager role, wherein the wearer role provides access to at least some of the stored data, and wherein the manager role provides access to at least the one or more rules associated with each role of the plurality of roles.

17. The wearable computing device of claim 16, wherein the wearer role further provides access to at least one rule of the one or more rules associated with each role of the plurality of roles.

18. The wearable computing device of claim 13, wherein at least one rule of the one or more rules regarding access to the portion of the stored data is related to providing aggregated data from the wearable computing device without providing identifying data about the wearer.

19. The wearable computing device of claim 13, further comprising a user interface configured for specifying at least one rule of the one or more rules regarding access to the portion of the stored data.

20. A non-transitory computer readable medium configured to store at least executable instructions, wherein the executable instructions, when executed by a processor of a wearable computing device, cause the wearable computing device to perform functions comprising:
obtaining, using one or more sensors on the wearable computing device, physiological parameters of a wearer of the wearable computing device, wherein the obtained physiological parameters comprise at least one of a pulse rate, breathing rate, blood pressure, skin temperature, or analyte concentration;
storing data on the wearable computing device, wherein the stored data comprises the obtained physiological parameters of the wearer of the wearable computing device;
after storing the data on the wearable computing device, receiving a request for a portion of the previously stored data;
determining a designated role associated with the request for the portion of the previously stored data;
determining one or more rules regarding access to the portion of the previously stored data based on the designated role; and
determining a response to the request for the portion of the previously stored data by at least:
determining whether the request is validated by at least applying the one or more rules to the request, and
after determining that the request is validated, providing the requested portion of the previously stored data.

* * * * *